United States Patent
Torchilin et al.

(10) Patent No.: US 8,685,538 B2
(45) Date of Patent: Apr. 1, 2014

(54) STABLE POLYELECTROLYTE COATED NANOPARTICLES

(75) Inventors: Vladimir Torchilin, Charlestown, MA (US); Yuri Lvov, Ruston, LA (US); Zhiguo Zheng, Ruston, LA (US)

(73) Assignees: Northeastern University, Boston, MA (US); Louisiana Tech University Research Foundation, a Division of Louisiana Tech University Foundation, Inc., Ruston, LA (US)

(*) Notice: Subject to any disclaimer, the term of this patent is extended or adjusted under 35 U.S.C. 154(b) by 0 days.

(21) Appl. No.: 13/259,320

(22) PCT Filed: Mar. 25, 2010

(86) PCT No.: PCT/US2010/028704
§ 371 (c)(1),
(2), (4) Date: Mar. 6, 2012

(87) PCT Pub. No.: WO2010/111517
PCT Pub. Date: Sep. 30, 2010

(65) Prior Publication Data
US 2012/0156499 A1    Jun. 21, 2012

Related U.S. Application Data

(60) Provisional application No. 61/163,145, filed on Mar. 25, 2009.

(51) Int. Cl.
*B32B 5/16* (2006.01)

(52) U.S. Cl.
USPC ........... 428/403; 428/407; 427/212; 427/214; 427/220

(58) Field of Classification Search
USPC .................. 428/403, 407; 427/212, 214, 220
See application file for complete search history.

(56) References Cited

U.S. PATENT DOCUMENTS

| | | |
|---|---|---|
| 2002/0187197 A1* | 12/2002 | Caruso et al. ................. 424/490 |
| 2005/0191491 A1 | 9/2005 | Wang et al. |
| 2007/0065387 A1 | 3/2007 | Beck et al. |
| 2008/0193543 A1* | 8/2008 | Morello et al. ............... 424/490 |

FOREIGN PATENT DOCUMENTS

| | | |
|---|---|---|
| WO | WO-00/33820 A2 | 6/2000 |
| WO | WO-2009/012303 A2 | 1/2009 |

OTHER PUBLICATIONS

International Search Report and Written Opinion mailed Jun. 3, 2010 for corresponding International Application PCT/US10/28704 (7 pgs.).
Torchilin, "Targeted polymeric micelles for delivery of poorly soluble drugs," CMLS Cellular and Molecular Life Sciences, Oct. 2004, vol. 61, No. 19-20, pp. 2549-2559.

* cited by examiner

*Primary Examiner* — Leszek Kiliman
(74) *Attorney, Agent, or Firm* — Wilmer Cutler Pickering Hale and Dorr LLP

(57) ABSTRACT

Stable nanoparticles comprising poorly soluble drugs are disclosed, as well as methods of making and methods of using such nanoparticles, e.g., as therapeutics and diagnostics.

19 Claims, 13 Drawing Sheets

STABLE POLYELECTROLYTE COATED NANOPARTICLES

CROSS REFERENCE TO RELATED APPLICATIONS

This application is a national stage application under 35 U.S.C. §371 of International Patent Application No. PCT/US2010/28704, designating the United States and filed on Mar. 25, 2010, which claims the benefit of priority to U.S. Provisional Application No. 61/163,145, filed Mar. 25, 2009, all of which are hereby incorporated by reference in their entirety.

FIELD OF THE INVENTION

The invention is in the field of medicine, and more specifically, to therapeutic nanoparticles for medical screening and treatment.

BACKGROUND OF THE INVENTION

Many potent drugs and drug candidates, especially anticancer drugs, are poorly soluble in water (e.g., tamoxifen, paclitaxel, and curcumin). Their poor solubility results in their low bioavailability and difficulties in preparing dosage forms.

Current attempts to solve this problem are associated with loading poorly soluble drugs (usually hydrophobic molecules) into various nanosized pharmaceutical carriers such as liposomes (drugs are loaded into the hydrophobic membrane of the liposome), micelles (drugs are loaded into the hydrophobic core of the micelle), and oil-in-water emulsions. However, many general problems are associated with these approaches, including relatively low loading efficacy of the drug into the nanocarrier (between 0.5% and 25% by weight, and often below 10% by weight) and sizes on the order of 200 nm to 300 nm.

SUMMARY OF THE INVENTION

The invention is based, at least in part, on the discovery of a method for making stable nanoparticles containing high concentrations of poorly water soluble drugs. This discovery was exploited to develop the invention, which, in one aspect, features a stable nanoparticle comprising a compound; and a polymeric coating comprising alternating polymeric layers of oppositely charged polymers; the nanoparticle having a diameter of about 10 nm to about 200 nm. In certain embodiments, the nanoparticle comprises two, three, four, five, or six polymeric layers of oppositely charged polymers.

In certain embodiments, the nanoparticle has a diameter of between about 10 nm and about 95 nm, between about 20 nm and about 90 nm, between about 30 nm and about 85 nm, between about 40 nm and about 80 nm, between about 50 nm and about 75 nm, between about 60 nm and about 70 nm, between about 90 nm and about 100 nm, between about 80 nm and about 100 nm, about 75 nm, about 80 nm, about 85 nm, about 90 nm, about 95 nm, or about 100 nm.

In other embodiments, the polymeric layers have a combined thickness of between about 2 nm and about 30 nm, between about 2 nm and about 25 nm, between about 2 nm and about 20 nm, between about 2 nm and about 15 nm, and between about 2 nm and about 10 nm.

In certain embodiments, the compound is present in the particle between about 5% by weight and about 95% by weight, between about 20% by weight and about 90% by weight, between about 40% by weight and about 85% by weight, between about 60% by weight and about 85% by weight, between about 75% by weight to about 90% by weight, and between about 80% by weight and about 90% by weight of the nanoparticle.

In some embodiments, the compound is a therapeutic compound described herein. In one embodiment, the compound is a cancer therapeutic described herein. In particular embodiments, the compound is tamoxifen, paclitaxel, atavaquone, or curcumin. In other embodiments, the compound is a low soluble anticancer drugs, camptothecin, topotecan, irinotecan, KRN 5500 (KRN), meso-tetraphenylporphine, dexamethasone, a benzodiazepine, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen. In some embodiments, the nanoparticle contains more than one type of compound.

In other embodiments, the compound is a detection agent described herein. In certain embodiments, the detection agent is a magnetic resonance imaging (MRI) contrast agent, a computed tomography (CT scan) imaging agent, an optical imaging agent, or a radioisotope.

In yet other embodiments, the polymers are selected from poly(dimethyldiallylamide ammonium chloride) (PDDA), poly(allylamine hydrochloride) (PAH), protamine sulfate (PS), poly(allylamine), poly(dimethyldiallyammonim chloride) polylysine, poly(ethylenimine), dextran amine, polyarginine, chitosan, gelatine A, sodium poly(styrene sulphonate) (PSS), human serum albumin (HSA), polyglutamic or alginic acids, poly(acrylic acid), poly(aspartic acid), poly (glutaric acid), dextran sulfate, carboxymethyl cellulose, hyaluronic acid, sodium alginate, gelatine B, chondroitin sulfate, and/or heparin. In certain embodiments, one or more polymers are biocompatible and/or biodegradable polymers.

In other embodiments, the compound is poorly soluble in water. In particular embodiments, the compound has a solubility in aqueous medium of less than about 10 mg/mL, of less than about 5 mg/mL, of less than about 2.5 mg/mL, of less than about 1 mg/mL, or of less than about 0.5 mg/mL.

In some embodiments, outermost polymeric layer is modified with a targeting agent. In certain embodiments, the targeting agent is an antibody. In particular embodiments, the antibody is an antibody against IL2 receptor a, complement system protein C5, CD11a, CD20, TNF-alpha, T cell CD3 receptor, T cell VLA4 receptor, F protein of RSV, epidermal growth factor receptor, vascular endothelial growth factor, glycoprotein IIb/IIIa, CD52, or epidermal growth factor receptor.

In some embodiments, the nanoparticle does not contain a detergent, surfactant, or oil.

In other embodiments, the compound is released from the nanoparticle at a rate of about 1%, about 2%, about 3%, about 4%, about 5%, about 6%, about 7%, about 8%, about 9%, about 10%, about 15%, about 20%, about 25%, about 30%, about 40%, about 50%, about 60%, about 70%, about 80%, about 90%, or about 95% in about an hour.

In another aspect, the invention features a stable nanoparticle comprising a compound or drug, and one or more bilayers comprising a first defined solid polymeric layer comprising a first polymer, the first layer surrounding the compound; and a second defined solid polymeric layer comprising a second polymer, the second layer surrounding the first layer, the first polymer and the second polymer having opposite charges, and the nanoparticle having a diameter of between about 10 nm and about 200 nm. In some embodiments, each layer can be composed of more than one polymer having similar isoelectric points.

In certain embodiments, the nanoparticle has a diameter of between about 10 nm and about 95 nm, between about 20 nm and about 90 nm, between about 30 nm and about 85 nm, between about 40 nm and about 80 nm, between about 50 nm and about 75 nm, between about 60 nm and about 70 nm, between about 90 nm and about 100 nm, between about 80 nm and about 100 nm, about 75 nm, about 80 nm, about 85 nm, about 90 nm, about 95 nm, or about 100 nm.

In certain embodiments, the compound is present in the nanoparticle between about 5% by weight and about 95% by weight, between about 20% by weight and about 90% by weight, between about 40% by weight and about 85% by weight, between about 60% by weight and about 85% by weight, between about 75% by weight to about 90% by weight, and between about 80% by weight and about 90% by weight of the nanoparticle.

In other embodiments, the first polymeric layer and the second polymeric layer have a combined thickness of between about 2 nm and about 30 nm, between about 2 nm and about 25 nm, between about 2 nm and about 20 nm, between about 2 nm and about 15 nm, and between about 2 nm and about 10 nm.

In certain embodiments, the first polymer is positively charged and the second polymer is negatively charged. In other embodiments, the first polymer is negatively charged and the second polymer is positively charged.

In some embodiments, the compound is a therapeutic compound described herein. In one embodiment, the compound is a cancer therapeutic described herein. In particular embodiments, the compound is tamoxifen, paclitaxel, atavaquone, or curcumin. In other embodiments, the compound is a low soluble anticancer drugs, camptothecin, topotecan, irinotecan, KRN 5500 (KRN), meso-tetraphenylporphine, dexamethasone, a benzodiazepine, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen. In some embodiments, the nanoparticle contains more than one type of compound.

In other embodiments, the compound is a detection agent described herein. In certain embodiments, the detection agent is a magnetic resonance imaging (MRI) contrast agent, a computed tomography (CT scan) imaging agent, an optical imaging agent, or a radioisotope.

In yet other embodiments, the first polymer is poly(dimethyldiallylamide ammonium chloride) (PDDA), poly(allylamine hydrochloride) (PAH), or protamine sulfate (PS). In certain embodiments, the first polymer is poly(allylamine), poly(dimethyldiallyammonim chloride) polylysine, poly (ethylenimine), poly(allylamine), dextran amine, polyarginine, chitosan, gelatine A, or protamine sulfate. In some embodiments, the second polymer is sodium poly(styrene sulphonate) (PSS) or human serum albumin (HSA). In particular embodiments, the second polymer is polyglutamic or alginic acids, poly(acrylic acid), poly(aspartic acid), poly (glutaric acid), dextran sulfate, carboxymethyl cellulose, hyaluronic acid, sodium alginate, gelatine B, chondroitin sulfate, and/or heparin.

In certain embodiments, the first polymer is a biocompatible and/or biodegradable polymer. In other embodiments, the second polymer is a biocompatible and/or biodegradable polymer. In other embodiments, both the first and the second polymer are biocompatible and/or biodegradable.

In yet other embodiments, the nanoparticle further comprises a third polymeric layer surrounding the second polymeric layer. In particular embodiments, the third polymeric layer comprises a third polymer having an opposite charge from the second polymer. In some embodiments, the third polymeric layer comprises PDDA. In certain embodiments, the first polymer and the third polymer are the same.

In other embodiments, the compound is poorly soluble in water. In particular embodiments, the compound has a solubility in aqueous medium of less than about 10 mg/mL, of less than about 5 mg/mL, of less than about 2.5 mg/mL, of less than about 1 mg/mL, or of less than about 0.5 mg/mL.

In some embodiments, outermost polymeric layer is modified with a targeting agent. In certain embodiments, the targeting agent is an antibody. In particular embodiments, the antibody is an antibody against IL2 receptor a, complement system protein C5, CD11a, CD20, TNF-alpha, T cell CD3 receptor, T cell VLA4 receptor, F protein of RSV, epidermal growth factor receptor, vascular endothelial growth factor, glycoprotein IIb/IIIa, CD52, or epidermal growth factor receptor.

In some embodiments, the nanoparticle does not contain a detergent, surfactant, or oil.

In other embodiments, the compound is released from the nanoparticle at a rate of about 1%, about 2%, about 3%, about 4%, about 5%, about 6%, about 7%, about 8%, about 9%, about 10%, about 15%, about 20%, about 25%, about 30%, about 40%, about 50%, about 60%, about 70%, about 80%, about 90%, or about 95% in about an hour.

In another aspect, the invention features a method of making a stable nanoparticle, the method comprising solubilizing a poorly soluble compound in an organic solvent; adding a first polymer in aqueous solution to the solubilized compound, the aqueous solution reducing the solubility of the compound in the organic solvent; and subjecting the compound to ultrasonication, the polymer added at a concentration sufficient to form a stable first polymeric layer around the compound.

In some embodiments, the method further comprises adding water to the solubilized compound and aqueous solution of the polymer at a rate and to a total volume sufficient to result in nucleation of the compound. In particular embodiments, nucleation occurs in the presence of ultrasonication. In certain embodiments, the nucleation is crystal or amorphous nucleation. In other embodiments, the solubilized compound is ultrasonicated at about 50 watts/cm$^2$ to about 500 watts/cm$^2$, about 75 watts/cm$^2$ to about 250 watts/cm$^2$, about 100 watts/cm$^2$ to about 200 watts/cm$^2$, or about 100 watts/cm$^2$ to about 150 watts/cm$^2$. In certain embodiments, the solubilized compound is ultrasonicated at a frequency of about 10 kHz to about 50 kHz, about 15 kHz to about 40 kHz, or about 20 kHz to about 30 kHz.

In yet other embodiments, the water is added at a rate of about 0.001 mL/min, about 0.005 mL/min, about 0.01 mL/min, about 0.025 mL/min, about 0.05 mL/min, about 0.1 mL/min, about 0.25 mL/min, about 0.5 mL/min, about 0.75 mL/min, about 1 mL/min, about 1.5 mL/min, about 2 mL/min, about 2.5 mL/min, about 3 mL/min, about 3.5 mL/min, about 4 mL/min, about 4.5 mL/min, or about 5 mL/min.

In particular embodiments, the total amount of water added is about 10% of the combined volume of the organic solvent and the aqueous solution of the polymer, about 20% of the combined volume, about 30% of the combined volume, about 40% of the combined volume, about 50% of the combined volume, about 60% of the combined volume, about 70% of the combined volume, about 80% of the combined volume, about 90% of the combined volume, about 100% of the combined volume, about 110% of the combined volume, about 120% of the combined volume, about 130% of the combined volume, about 140% of the combined volume, about 150% of the combined volume, about 160% of the combined volume, about 170% of the combined volume, about 180% of the combined volume, about 190% of the combined volume, about 200% of the combined volume, about 250% of the combined volume, about 300% of the combined volume, about 400% of the combined volume, or about 500% or more of the combined volume of the organic solvent and the aqueous solution of the polymer.

In other embodiments, the organic solvent is toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, propylene glycol, polyethylene glycol, ethanol, dimethyl sulfoxide, N-methyl-2-pyrrolidone, glycofurol, Solketal™, glycerol formal, acetone, tetrahydrofurfuryl alcohol, diglyme, dimethyl isosorbide, or ethyl lactate.

In certain embodiments, the aqueous solution reduces the solubility of the compound in the organic solvent by about 10%, about 20%, about 30%, about 40%, about 50%, about 60%, about 70%, about 80%, about 90%, about 95%, or about 100%, compared to the solubility of the compound in the organic solvent in the absence of the aqueous solution.

In yet other embodiments, the polymer is added at a concentration of about 0.05 mg/mL, about 0.1 mg/mL, about 0.5 mg/mL, about 1 mg/mL, about 1.5 mg/mL, about 2 mg/mL, about 2.5 mg/mL, about 3 mg/mL, about 4 mg/mL, about 5 mg/mL, about 7.5 mg/mL, about 10 mg/mL, or more.

In some embodiments, the solubilized compound has a negative charge. In other embodiments, the polymer added to the compound has a positive charge.

In certain embodiments, the nanoparticle has a diameter of between about 10 nm and about 200 nm, between about 20 nm and about 100 nm, between about 30 nm and about 90 nm, between about 40 nm and about 80 nm, between about 50 nm and about 75 nm, between about 60 nm and about 70 nm, between about 90 nm and about 100 nm, between about 80 nm and about 100 nm, about 75 nm, about 80 nm, about 85 nm, about 90 nm, about 95 nm, or about 100 nm.

In other embodiments, the compound is poorly soluble in water. In particular embodiments, the compound has a solubility in aqueous medium of less than about 10 mg/mL, of less than about 5 mg/mL, of less than about 2.5 mg/mL, of less than about 1 mg/mL, or of less than about 0.5 mg/mL.

In certain embodiments, the compound is present in the nanoparticle between about 5% by weight and about 95% by weight, between about 20% by weight and about 90% by weight, between about 40% by weight and about 85% by weight, between about 60% by weight and about 85% by weight, between about 75% by weight to about 90% by weight, and between about 80% by weight and about 90% by weight of the nanoparticle.

In other embodiments, the first polymer is poly(dimethyldiallylamide ammonium chloride) (PDDA), poly(allylamine hydrochloride) (PAH), or protamine sulfate (PS). In particular embodiments, the method further comprising adding a second polymer to the nanoparticle after the first polymeric layer is formed, to form a second polymeric layer surrounding the first polymeric layer. In some embodiments, the second polymer is sodium poly(styrene sulphonate) (PSS) or human serum albumin (HSA). In yet other embodiments, the method further comprises adding additional oppositely charged polymers to the nanoparticle, forming additional polymeric layers.

In some embodiments, the compound is a therapeutic compound described herein. In one embodiment, the compound is a cancer therapeutic described herein. In particular embodiments, the compound is tamoxifen, paclitaxel, atavaquone, or curcumin. In other embodiments, the compound is a low soluble anticancer drugs, camptothecin, topotecan, irinotecan, KRN 5500 (KRN), meso-tetraphenylporphine, dexamethasone, a benzodiazepine, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen. In some embodiments, the nanoparticle contains more than one type of compound.

In other embodiments, the compound is a detection agent described herein. In certain embodiments, the detection agent is a magnetic resonance imaging (MRI) contrast agent, a computed tomography (CT scan) imaging agent, an optical imaging agent, or a radioisotope.

In some embodiments, the method further comprises attaching a targeting agent to the outermost polymeric layer. In certain embodiments, the targeting agent is an antibody. In particular embodiments, the antibody is an antibody against IL2 receptor a, complement system protein C5, CD11a, CD20, TNF-alpha, T cell CD3 receptor, T cell VLA4 receptor, F protein of RSV, epidermal growth factor receptor, vascular endothelial growth factor, glycoprotein IIb/IIIa, CD52, or epidermal growth factor receptor.

In another aspect, the invention features a nanoparticle produced by any method described herein.

In another aspect, the invention features a method of treating a subject having a disease or disorder described herein, the method comprising administering to the subject a nanoparticle described herein in an amount sufficient to treat the disease or the disorder.

In some embodiments, the subject is a vertebrate. In certain embodiments, the subject is a mammal. In particular embodiments, the subject is a human.

In yet another aspect, the invention features a method of treating a subject having a tumor, the method comprising administering to the subject a nanoparticle described herein in an amount sufficient to reduce tumor size or number of tumor cells, wherein the nanoparticle comprises a cancer therapeutic agent described herein. In particular embodiments, the cancer therapeutic agent is paclitaxel, tamoxifen, or curcumin.

In some embodiments, the subject is a vertebrate. In certain embodiments, the subject is a mammal. In particular embodiments, the subject is a human.

In another aspect, the invention features the use of a nanoparticle according to any of the aspects described herein, for the treatment of a disease or a disorder described herein.

The following figures are presented for the purpose of illustration only, and are not intended to be limiting.

DETAILED DESCRIPTION OF THE INVENTION

Figure 1:
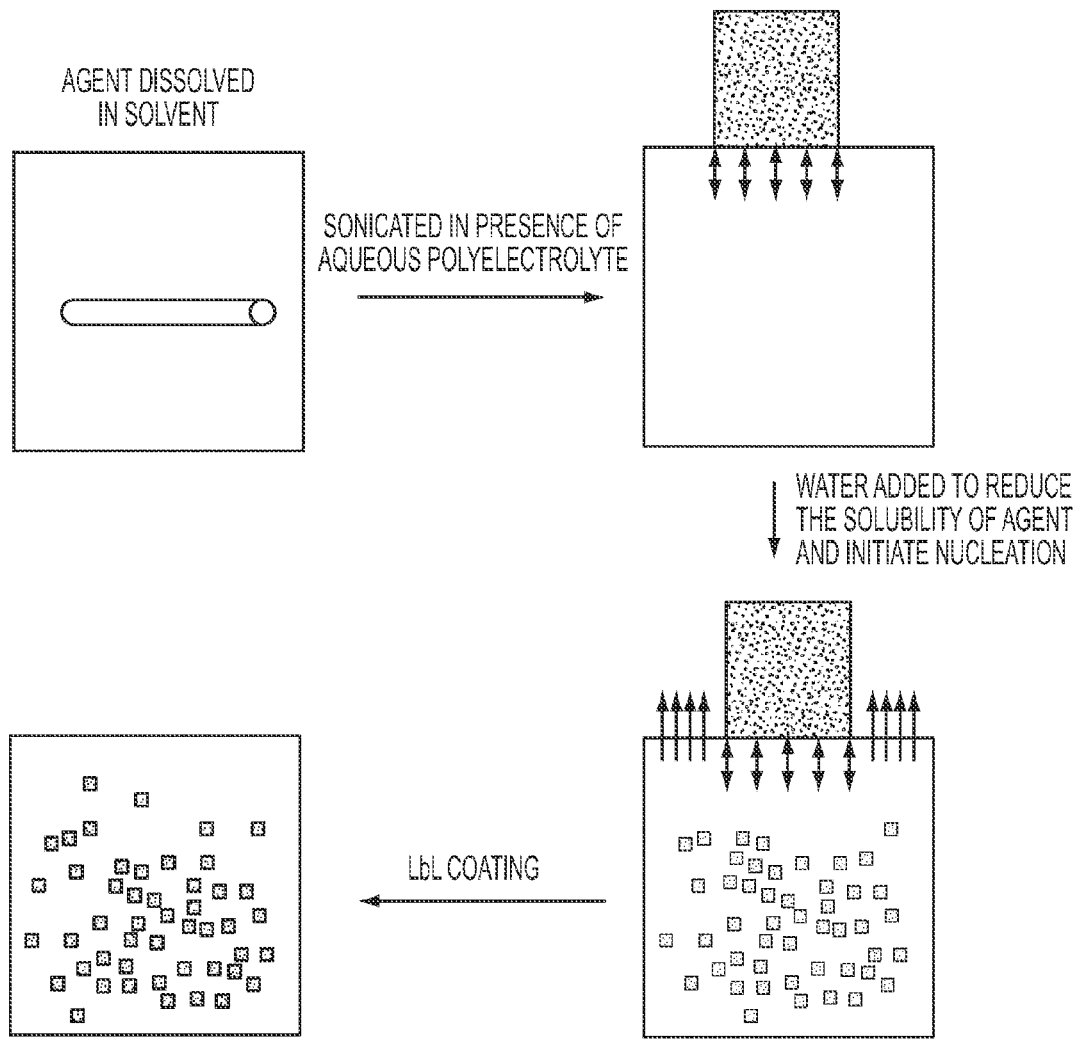
FIG. 1 is a schematic illustration of an exemplary method for making a nanoparticle.

All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Other features and advantages of the invention will be apparent from the following detailed description, and from the claims.

DEFINITIONS

As used herein, a "subject" is a mammal, e.g., a human, mouse, rat, guinea pig, dog, cat, horse, cow, pig, or non-human primate, such as a monkey, chimpanzee, baboon or rhesus.

As used herein, the term "biodegradable" refers to a substance that can be decomposed (e.g., chemically or enzymatically) or broken down in component molecules by natural biological processes (e.g., in vertebrate animals such as humans).

As used herein, the term "biocompatible" refers to a substance that has no unintended toxic or injurious effects on biological functions in a target organism.

The term "targeting agent" refers to a ligand or molecule capable of specifically or selectively (i.e., non-randomly) binding or hybridizing to, or otherwise interacting with, a desired target molecule. Examples of targeting agents include, but are not limited to, nucleic acid molecules (e.g., RNA and DNA, including ligand-binding RNA molecules such as aptamers, antisense, or ribozymes), polypeptides (e.g., antigen binding proteins, receptor ligands, signal peptides, and hydrophobic membrane spanning domains), antibodies (and portions thereof), organic molecules (e.g., biotin, carbohydrates, and glycoproteins), and inorganic molecules (e.g., vitamins). A nanoparticle described herein can have affixed thereto one or more of a variety of such targeting agents.

As used herein, the term "nanoparticle" refers to a particle having a diameter in the range of about 10 nm to about 200 nm. Nanoparticles include particles capable of containing a therapeutic or diagnostic agent that can be released within a subject. The terms "nanoparticle" and "nanocolloids" are used interchangeably herein.

The term "about", as used herein, means a numeric value having a range of ±10% around the cited value.

As used herein, "treat," "treating" or "treatment" refers to administering a therapy in an amount, manner (e.g., schedule of administration), and/or mode (e.g., route of administration), effective to improve a disorder (e.g., a disorder described herein) or a symptom thereof, or to prevent or slow the progression of a disorder (e.g., a disorder described herein) or a symptom thereof. This can be evidenced by, e.g., an improvement in a parameter associated with a disorder or a symptom thereof, e.g., to a statistically significant degree or to a degree detectable to one skilled in the art. An effective amount, manner, or mode can vary depending on the subject and may be tailored to the subject. By preventing or slowing progression of a disorder or a symptom thereof, a treatment can prevent or slow deterioration resulting from a disorder or a symptom thereof in an affected or diagnosed subject.

As used herein, a "solid" layer refers to a defined firm border between a compound within a nanoparticle and the environment external to the compound. For example, nanoparticles described herein can have one or more solid polymeric layers that reduce or restrict the access of external molecules to the compound at the core of the nanoparticle.

The term "polymer," as used herein, refers to a molecule composed of repeated subunits. Such molecules include, but are not limited to, polypeptides, polynucleotides, polysaccharides and polyalkylene glycols. Polymers can also be biodegradable and/or biocompatible.

The terms "polypeptide," "peptide," and "protein" are used interchangeably herein and refer to a polymer of amino acid residues. The terms apply to naturally occurring amino acid polymers as well as amino acid polymers in which one or more amino acid residues are non-natural amino acids. Additionally, such polypeptides, peptides, and proteins include amino acid chains of any length, including full length proteins, wherein the amino acid residues are linked by covalent peptide bonds.

The term "stable", as used herein, means that, for a period of at least six months after the nanoparticles are made, a majority of the nanoparticles remain intact at RT in a non-suspended form or as a dry pellet.

As used herein, a compound that is "poorly soluble," when referring to a compound, means a compound that has a solubility in aqueous medium of less than about 10 mg/mL, such as less than about 1 mg/mL.

The terms "drug," and "therapeutic agent" are used interchangeably herein and refer to any substance used in the prevention, diagnosis, alleviation, treatment, or cure of a disease or condition.

As used herein, "zeta potential" means the electric potential across an ion layer, e.g., a charged polymeric layer, around a charged colloidal nanoparticle.

The term "surrounding" is used herein to mean enclosing, enveloping, encompassing, or extending around at least a portion of the drug or compound or interior layer.

The term "ultrasonication", as used herein, means a process of applying sonic waves to a sample, such as a solution. The sonic waves can have a wave frequency of about 10 kHz to about 50 kHz and a sonicator power of about 50 Wt/cm$^2$ of the surface to about 500 Wt/cm$^2$ of the surface.

As used herein, the term "organic solvent" refers to a carbon-containing chemical, generally in liquid form, used to dissolve another substance. Examples of organic solvents include, but are not limited to, alcohols, glycols, ethers, dimethoxyethane, acetone, chloroform, dimethyl sulfoxide, hexane, toluene, tetrahydrofuron (THF), methylene chloride and the like.

The methods described herein use, in part, organic solvents to solubilize poorly soluble compounds and sonication in the presence of a polyelectrolyte to make stable nanocolloids of poorly soluble drugs. In addition, layer-by-layer ("LbL") methods can be used to form additional coatings on the nanoparticles.

An exemplary method is depicted schematically in FIG. 1. As shown in FIG. 1, a compound is initially dissolved in an organic solvent. Any suitable organic solvent can be used. Nonlimiting examples of organic solvents include, e.g., toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, propylene glycol, polyethylene glycols, ethanol, dimethyl sulfoxide, N-methyl-2-pyrrolidone, glycofurol, Solketal™, glycerol formal, acetone, tetrahydrofurfuryl alcohol, diglyme, dimethyl isosorbide, and ethyl lactate.

Once the compound is dissolved in the organic solvent, a water soluble polymer (polycation or polyanion) is added to the solution, and the solution is subjected to ultrasonication. Any water soluble polymer described herein can be used. For example, if the compound dissolved in the organic solvent is negatively charged, a polycation polymer can be added to the organic solution.

The solution can be subjected to a range of ultrasonication using, e.g., commercially available systems (such as those available from Hielscher USA, Inc., Ringwood, N.J.; and M P Interconsulting, Marais, Switzerland). The ultrasonication can be performed at a suitable range of power (e.g., from about 50 watts/cm$^2$ to about 3000 watts/cm$^2$) and frequency (e.g., from about 10 kHz to about 50 kHz).

During ultrasonication, water is slowly added to the solution, and the solubility of the compound decreases. Water is added until a supersaturated solution of the compound is achieved, and crystal nucleation commences. In the presence of ultrasonication, particle growth is restricted, and the water soluble polymer is adsorbed onto the compound nanocrystal. The polymer forms a very thin, but stable, polymeric layer or shell around each nanocrystal of the compound. This results in a nanoparticle containing the compound and having a layer of the polymer surrounding the compound. The size of the nanoparticle can be on the order of a few nanometers (e.g., between about 2 nm and about 100 nm, between about 10 nm and about 100 nm, between about 20 nm and about 75 nm, between about 30 nm and about 75 nm, between about 40 nm and about 60 nm, between about 50 nm and about 100 nm, between about 60 nm and about 100 nm, between about 70 nm and about 100 nm, between about 80 nm and about 100 nm, or between about 90 nm and about 100 nm).

As shown in FIG. 1, the first polymer layer can then be further stabilized by the addition of another, oppositely-charged polymer, which forms a firm electrostatic complex with the first layer (i.e., a "bilayer"). This results in the appearance of a very thin, but stable, polymeric layer or shell around each nanoparticle of a compound. This shell can prevent particle agglomeration, and can be easily and reproducibly formed on the surface of any compound particle. By varying the charge density on each polymer, or the number of coating cycles, drug nanoparticles can be prepared with a different surface charge and different thickness of the polymeric coat. This, in turn, provides a way to control drug release from such particles. The LbL process includes the formation of alternate outermost layers of opposite charge at every adsorption cycle. An alternate assembly of linear polyanions and polycations can add about 1-2 nm for a single bilayer, and a number of bilayers, which can be built up, can vary from one to few hundreds.

Polymers

The nanoparticles described herein can be produced by encapsulating a compound described herein within one or more layers of polyelectrolytes (or polymers), creating a defined polymeric layer. In some instances, polycation polymers are used. Such polycation polymers include, without limitation, poly(allylamine), poly(dimethyldiallyammonim chloride) polylysine, poly(ethylenimine), poly(allylamine), and natural polycations such as dextran amine, polyarginine, chitosan, gelatine A, and/or protamine sulfate. In other instances, polyanion polymers are used, including, without limitation, poly(styrenesulfonate), polyglutamic or alginic acids, poly(acrylic acid), poly(aspartic acid), poly(glutaric acid), and natural polyelectrolytes with similar ionized groups such as dextran sulfate, carboxymethyl cellulose, hyaluronic acid, sodium alginate, gelatine B, chondroitin sulfate, and/or heparin. These polymers can be synthesized, isolated, or commercially obtained.

In certain instances, biodegradable and/or biocompatible polymers are used. These include, without limitation, substantially pure carbon lattices (e.g., graphite), dextran, polysaccharides, polypeptides, polynucleotides, acrylate gels, polyanhydride, poly(lactide-co-glycolide), polytetrafluoroethylene, polyhydroxyalkonates, cross-linked alginates, gelatin, collagen, cross-linked collagen, collagen derivatives (such as succinylated collagen or methylated collagen), cross-linked hyaluronic acid, chitosan, chitosan derivatives (such as methylpyrrolidone-chitosan), cellulose and cellulose derivatives (such as cellulose acetate or carboxymethyl cellulose), dextran derivatives (such carboxymethyl dextran), starch and derivatives of starch (such as hydroxyethyl starch), other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyglycolide homoploymers, polyoxanones and polyoxalates, copolymer of poly(bis(p-carboxyphenoxy)propane)anhydride (PCPP) and sebacic acid, poly(l-glutamic acid), poly(d-glutamic acid), polyacrylic acid, poly(dl-glutamic acid), poly (l-aspartic acid), poly(d-aspartic acid), poly(dl-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin, silicone rubbers, or polyurethanes, and the like. Other biodegradable materials that can be used include naturally derived polymers, such as acacia, gelatin, dextrans, albumins, alginates/starch, and the like; or synthetic polymers, whether hydrophilic or hydrophobic. The materials can be synthesized, isolated, and are commercially available.

Therapeutic and Detection Agents

A nanoparticle fabricated using a method described herein can be modified with many types of compounds, such as, but not limited to, therapeutic or detection agents. The nanoparticle is modified by attaching an agent to a surface of a nanoparticle, such as an outer surface.

Nonlimiting examples of therapeutic agents useful for attaching to a nanoparticle include, e.g., steroids, analgesics, local anesthetics, antibiotic agents, chemotherapeutic agents, immunosuppressive agents, anti-inflammatory agents, anti-proliferative agents, antimitotic agents, angiogenic agents, antipsychotic agents, central nervous system (CNS) agents, anticoagulants, fibrinolytic agents, growth factors, antibodies, ocular drugs, and metabolites, analogs, derivatives, fragments, and purified, isolated, recombinant and chemically synthesized versions of these species, and combinations thereof.

Representative useful therapeutic agents include, but are not limited to, tamoxifen, paclitaxel, low soluble anticancer drugs, camptothecin and its derivatives, e.g., topotecan and irinotecan, KRN 5500 (KRN), meso-tetraphenylporphine, dexamethasone, benzodiazepines, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen, as well as all mainstream antibiotics, including the penicillin group, fluoroquinolones, and first, second, third, and fourth generation cephalosporins. These agents are commercially available from, e.g., Merck & Co., Barr Laboratories, Avalon Pharma, and Sun Pharma, among others.

In some instances, the nanoparticles described herein can be used to detect or image cells, e.g., using nanoparticles coupled to a detection agent. The detection agent can be used to qualitatively or quantitatively analyze the location and/or the amount of a nanoparticle at a particular locus. The detection agent can also be used to image a nanoparticle and/or a cell or tissue target of a nanoparticle using standard methods.

In some instances, the nanoparticles are modified or derivatized (or labeled) with a detection agent. Examples of detection agents include magnetic resonance imaging (MRI) contrast agents, computed tomography (CT scan) imaging agents, optical imaging agents and radioisotopes. Nonlimiting examples of detection agents include, without limitation, fluorescent compounds, various enzymes, prosthetic groups, luminescent materials, bioluminescent materials, fluorescent emitting metal atoms, (e.g., europium (Eu)), radioactive isotopes (described below), quantum dots, electron-dense reagents, and haptens. The detection reagent can be detected using various means including, but not limited to, spectroscopic, photochemical, radiochemical, biochemical, immunochemical, or chemical means.

Nonlimiting exemplary fluorescent detection agents include fluorescein, fluorescein isothiocyanate, rhodamine, 5-dimethylamine-1-napthalenesulfonyl chloride, phycoerythrin, and the like. A detection agent can also be a detectable enzyme, such as alkaline phosphatase, horseradish peroxidase, β-galactosidase, acetylcholinesterase, glucose oxidase and the like. When a nanoparticle is derivatized with a detectable enzyme, it can be detected by adding additional reagents that the enzyme uses to produce a detectable reaction product. For example, when the detection agent is horseradish peroxidase, the addition of hydrogen peroxide and diaminobenzidine leads to a detectable colored reaction product. A nanoparticle can also be derivatized with a prosthetic group (e.g., streptavidin/biotin and avidin/biotin). For example, a nanoparticle can be derivatized with biotin and detected through indirect measurement of avidin or streptavidin binding. Nonlimiting examples of fluorescent compounds that can be used as detection reagents include umbelliferone, fluorescein, fluorescein isothiocyanate, rhodamine, dichlorotriazinylamine fluorescein, dansyl chloride, and phycoerythrin. Luminescent materials include, e.g., luminol, and bioluminescent materials include, e.g., luciferase, luciferin, and aequorin.

A detection agent useful for modification of the nanoparticle can also be a radioactive isotope, such as, but not limited to, α-, β-, or γ-emitters; or β- and γ-emitters. Radioactive isotopes can be used in diagnostic or therapeutic applications. Such radioactive isotopes include, but are not limited to, iodine ($^{131}$I or $^{125}$I), yttrium ($^{90}$Y), lutetium ($^{177}$Lu), actinium ($^{225}$Ac), praseodymium ($^{142}$Pr or $^{143}$Pr), astatine ($^{211}$At), rhenium ($^{186}$Re or $^{187}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$S), and gallium ($^{67}$Ga).

The nanoparticle can be radiolabeled using techniques known in the art. In some situations, a nanoparticle described herein is contacted with a chelating agent, e.g., 1,4,7,10-tetraazacyclododecane-N,N',N'',N'''-tetraacetic acid (DOTA), to thereby produce a conjugated nanoparticle. The conjugated nanoparticle is then radiolabeled with a radioisotope, e.g., $^{111}$In, $^{90}$Y, $^{117}$Lu, $^{186}$Re, or $^{99m}$Tc, to thereby produce a labeled nanoparticle. In other methods, the nanoparticles can be labeled with $^{111}$In and $^{90}$Y using weak transchelators such as citrate (see, e.g., Khaw et al., *Science* 209:295-297 (1980)) or $^{99m}$Tc after reduction in reducing agents such as Na Dithionite (see, e.g., Khaw et al., *J. Nucl. Med.* 23:1011-1019 (1982)) or by SnCl$_2$ reduction (see, e.g., Khaw et al., *J. Nucl. Med.* 47:868-876 (2006)). Other methods are described in, e.g., Lindegren et al., *Bioconjug. Chem.* 13:502-509 (2002); Boyd et al., *Mol. Pharm.* 3:614-627 (2006); and del Rosario et al., *J. Nucl. Med.* 34:1147-1151 (1993).

Targeting Agents

In some instances, a nanoparticle described herein includes a targeting agent that is attached, fixed, or conjugated to, the nanoparticle, such as the outermost surface of the nanoparticle. In certain situations, the targeting agent specifically binds to a particular biological target. Nonlimiting examples of biological targets include tumor cells, bacteria, viruses, cell surface proteins, cell surface receptors, cell surface polysaccharides, extracellular matrix proteins, intracellular proteins and intracellular nucleic acids. The targeting agents can be, for example, various specific ligands, such as antibodies, monoclonal antibodies and their fragments, folate, mannose, galactose and other mono-, di-, and oligosaccharides, and RGD peptide.

The nanoparticles and methods described herein are not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to receptors. In some instances, a nanoparticle described herein can be conjugated to one, two, or more of a variety of targeting agents. For example, when two or more targeting agents are used, the targeting agents can be similar or dissimilar. Utilization of more than one targeting agent on a particular nanoparticle can allow the targeting of multiple biological targets or can increase the affinity for a particular target.

The targeting agents can be associated with the nanoparticles in a number of ways. For example, the targeting agents can be associated (e.g., covalently or noncovalently bound) to other subcomponents/elements of the nanoparticle with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages. Alternatively, such agents can be directly conjugated to the outer surface of a nanoparticle.

In addition, a nanoparticle can also incorporate reactive groups (e.g., amine groups such as polylysine, dextranemine, profamine sulfate, and/or chitosan). The reactive group can allow for further attachment of various specific ligands or reporter groups (e.g., $^{125}$I, $^{131}$I, I, Br, various chelating groups such as DTPA, which can be loaded with reporter heavy metals such as $^{111}$In, $^{99m}$Tc, GD, Mn, fluorescent groups such as FITC, rhodamine, Alexa, and quantum dots), and/or other moieties (e.g., ligands, antibodies, and/or portions thereof).

Antibodies as Targeting Agents

In some instances, the targeting agents are antigen binding proteins or antibodies or binding portions thereof. Antibodies can be generated to allow for the specific targeting of antigens or immunogens (e.g., tumor, tissue, or pathogen specific antigens) on various biological targets (e.g., pathogens, tumor cells, normal tissue). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv).

Methods of making and using polyclonal and monoclonal antibodies are well known in the art, e.g., in Harlow et al., *Using Antibodies: A Laboratory Manual: Portable Protocol I*. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

Antibody attachment to nanoparticles can be performed through standard covalent binding to free amine groups (see, e.g., Torchilin et al. (1987) *Hybridoma*, 6:229-240; Torchilin, et al., (2001)*Biochim. Biophys. Acta*, 1511:397-411; Masuko, et al., (2005), *Biomacromol.*, 6:800-884) in the outermost surface of the nanoparticle. Standard methods of protein covalent binding are known, such as covalent binding through amine groups. This methodology can be found in, e.g., *Protein Architecture: Interfacing Molecular Assemblies and Immobilization*, editors: Lvov et al. (2000) Chapter 2, pp. 25-54. In certain instances, the outer surface of the nanoparticle can be functionalized with a polymer that has free amino, carboxy, SH—, epoxy-, and/or other groups that can react with ligand molecules directly or after preliminary activation with, e.g., carbodiimides, SPDP, SMCC, and/or other mono- and bifunctional reagents.

Signal Peptides as Targeting Agents

In some instances, the targeting agents include a signal peptide. These peptides can be chemically synthesized or cloned, expressed and purified using known techniques. Signal peptides can be used to target the nanoparticles described herein to a discreet region within a cell. In some situations, specific amino acid sequences are responsible for targeting the nanoparticles into cellular organelles and compartments. For example, the signal peptides can direct a nanoparticle described herein into mitochondria. In other examples, a nuclear localization signal is used.

Nucleic Acids as Targeting Agents

In other instances, the targeting agent is a nucleic acid (e.g., RNA or DNA). In some examples, the nucleic acid targeting agents are designed to hybridize by base pairing to a particular nucleic acid (e.g., chromosomal DNA, mRNA, or ribosomal RNA). In other situations, the nucleic acids bind a ligand or biological target. For example, the nucleic acid can bind reverse transcriptase, Rev or Tat proteins of HIV (Tuerk et al., *Gene*, 137(1):33-9 (1993)); human nerve growth factor (Binkley et al., *Nuc. Acids Res.*, 23(16):3198-205 (1995)); or vascular endothelial growth factor (Jellinek et al., *Biochem.*, 83(34): 10450-6 (1994)). Nucleic acids that bind ligands can be identified by known methods, such as the SELEX procedure (see, e.g., U.S. Pat. Nos. 5,475,096; 5,270,163; and 5,475,096; and WO 97/38134; WO 98/33941; and WO 99/07724). The targeting agents can also be aptamers that bind to particular sequences.

Other Targeting Agents

The targeting agents can recognize a variety of epitopes on preselected biological targets (e.g., pathogens, tumor cells, or normal cells). For example, in some instances, the targeting agent can be sialic acid to target HIV (Wies et al., *Nature*, 333:426 (1988)), influenza (White et al., *Cell*, 56:725 (1989)), *Chlamydia* (*Infect. Immunol*, 57:2378 (1989)), *Neisseria meningitidis, Streptococcus suis, Salmonella*, mumps, newcastle, reovirus, Sendai virus, and myxovirus; and 9-OAC sialic acid to target coronavirus, encephalomyelitis virus, and rotavirus; non-sialic acid glycoproteins to target cytomegalovirus (*Virology*, 176:337 (1990)) and measles virus (*Virology*, 172:386 (1989)); CD4 (Khatzman et al., *Nature*, 312:763 (1985)), vasoactive intestinal peptide (Sacerdote et al., *J. of Neuroscience Research*, 18:102 (1987)), and peptide T (Ruff et al., *FEBS Letters*, 211:17 (1987)) to target HIV; epidermal growth factor to target vaccinia (Epstein et al., *Nature*, 318: 663 (1985)); acetylcholine receptor to target rabies (Lentz et al., *Science* 215: 182 (1982)); Cd3 complement receptor to target Epstein-Barr virus (Carel et al., *J. Biol. Chem.*, 265: 12293 (1990)); .beta.-adrenergic receptor to target reovirus (Co et al., *Proc. Natl. Acad. Sci. USA*, 82:1494 (1985)); ICAM-1 (Marlin et al., *Nature*, 344:70 (1990)), N-CAM, and myelin-associated glycoprotein MAb (Shephey et al., *Proc. Natl. Acad. Sci. USA*, 85:7743 (1988)) to target rhinovirus; polio virus receptor to target polio virus (Mendelsohn et al., *Cell*, 56:855 (1989)); fibroblast growth factor receptor to target herpes virus (Kaner et al., *Science,* 248:1410 (1990)); oligomannose to target *Escherichia coli;* and ganglioside $G_{M1}$ to target *Neisseria meningitides.*

In other instances, the targeting agent targets nanoparticles to factors expressed by oncogenes. These can include, but are not limited to, tyrosine kinases (membrane-associated and cytoplasmic forms), such as members of the Src family; serine/threonine kinases, such as Mos; growth factor and receptors, such as platelet derived growth factor (PDDG), SMALL GTPases (G proteins), including the ras family, cyclin-dependent protein kinases (cdk), members of the myc family members, including c-myc, N-myc, and L-myc, and bcl-2 family members.

In addition, vitamins (both fat soluble and non-fat soluble vitamins) can be used as targeting agents to target biological targets (e.g., cells) that have receptors for, or otherwise take up, vitamins. For example, fat soluble vitamins (such as vitamin D and its analogs, vitamin E, vitamin A), and water soluble vitamins (such as vitamin C) can be used as targeting agents.

Therapeutic Administration

The nanoparticles described herein can be used to treat (e.g., mediate the translocation of drugs into) diseased cells and tissues. In this regard, various diseases are amenable to treatment using the nanoparticles and methods described herein. Exemplary, nonlimiting diseases that can be treated with the nanoparticles include cancers such as, but not limited to, breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; non-Hodgkins lymphoma, multiple sclerosis, neuroblastoma and glioblastoma; T and B cell mediated autoimmune diseases; inflammatory diseases; infections; hyperproliferative diseases; AIDS; degenerative conditions, cardiovascular diseases, transplant rejection, and the like. In some cases, the treated cancer cells are metastatic.

The route and/or mode of administration of a nanoparticle described herein can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner.

In some instances, a nanoparticle described herein is administered locally. This is achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, a nanoparticle described herein is introduced into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

This disclosure also features a device for administering a nanoparticle described herein. The device can include, e.g., one or more housings for storing pharmaceutical compositions, and can be configured to deliver unit doses of a nanoparticle described herein.

Pulmonary administration can also be employed, e.g., by use of an inhaler or nebulizer, and formulation with an aerosolizing agent, or via perfusion in a fluorocarbon or synthetic pulmonary surfactant.

In some instances, a nanoparticle described herein can be delivered in a vesicle, in particular, a liposome (see Langer, *Science* 249:1527-1533 (1990) and Treat et al., *Liposomes in the Therapy of Infectious Disease and Cancer* pp. 317-327 and pp. 353-365 (1989)).

In yet other situations, a nanoparticle described herein can be delivered in a controlled-release system or sustained-release system (see, e.g., Goodson, in *Medical Applications of Controlled Release,* vol. 2, pp. 115-138 (1984)). Other controlled or sustained-release systems discussed in the review by Langer, *Science* 249:1527-1533 (1990) can be used. In one case, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., N. Engl. *J. Med.* 321:574 (1989)).

In yet other situations, a controlled- or sustained-release system can be placed in proximity of a target of nanoparticle described herein, reducing the dose to a fraction of the systemic dose.

A nanoparticle described herein can be formulated as a pharmaceutical composition that includes a suitable amount of a physiologically acceptable excipient (see, e.g., *Remington's Pharmaceutical Sciences pp.* 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Water is a particularly useful excipient when a nanoparticle described herein is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in *Remington's Pharmaceutical Sciences pp.* 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. A nanoparticle described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, a nanoparticle described herein is formulated for intravenous administration. Compositions for intravenous administration can comprise a sterile isotonic aqueous buffer. The compositions can also include a solubilizing agent. Compositions for intravenous administration can optionally include a local anesthetic such as lignocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where a nanoparticle described herein is administered by infusion, it can be dispensed, for example, with an infusion bottle containing sterile pharmaceutical grade water or saline. Where a nanoparticle described herein is administered by injection, an ampule of sterile water for injection or saline can be provided so that the ingredients can be mixed prior to administration.

In other circumstances, a nanoparticle described herein can be administered across the surface of the body and the inner linings of the bodily passages, including epithelial and mucosal tissues. Such administrations can be carried out using a nanoparticle described herein in lotions, creams, foams, patches, suspensions, solutions, and suppositories (e.g., rectal or vaginal). In some instances, a transdermal patch can be used that contains a nanoparticle described herein and a carrier that is inert to the nanoparticle described herein, is non-toxic to the skin, and that allows delivery of the agent for systemic absorption into the blood stream via the skin. The carrier can take any number of forms such as creams or ointments, pastes, gels, or occlusive devices. The creams or ointments can be viscous liquid or semisolid emulsions of either the oil-in-water or water-in-oil type. Pastes of absorptive powders dispersed in petroleum or hydrophilic petroleum containing a nanoparticle described herein can also be used. A variety of occlusive devices can be used to release a nanoparticle described herein into the blood stream, such as a semipermeable membrane covering a reservoir containing the nanoparticle with or without a carrier, or a matrix containing the nanoparticle.

A nanoparticle described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of a nanoparticle described herein that is effective for treating disorder or disease can be determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. For example, the dose of a nanoparticle described herein can each range from about 0.001 mg/kg to about 250 mg/kg of body weight per day, from about 1 mg/kg to about 250 mg/kg body weight per day, from about 1 mg/kg to about 50 mg/kg body weight per day, or from about 1 mg/kg to about 20 mg/kg of body weight per day. Equivalent dosages can be administered over various time periods including, but not limited to, about every 2 hrs, about every 6 hrs, about every 8 hrs, about every 12 hrs, about every 24 hrs, about every 36 hrs, about every 48 hrs, about every 72 hrs, about every week, about every two weeks, about every three weeks, about every month, and about every two months. The number and frequency of dosages corresponding to a completed course of therapy can be determined according to the judgment of a health-care practitioner.

In some instances, a pharmaceutical composition described herein is in unit dosage form, e.g., as a tablet, capsule, powder, solution, suspension, emulsion, granule, or suppository. In such form, the pharmaceutical composition can be sub-divided into unit doses containing appropriate quantities of a nanoparticle described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Kits

A nanoparticle described herein can be provided in a kit. In some instances, the kit includes (a) a container that contains a nanoparticle and, optionally (b) informational material. The informational material can be descriptive, instructional, marketing or other material that relates to the methods described herein and/or the use of the nanoparticles, e.g., for therapeutic benefit.

The informational material of the kits is not limited in its form. In some instances, the informational material can include information about production of the nanoparticle, molecular weight of the nanoparticle, concentration, date of expiration, batch or production site information, and so forth. In other situations, the informational material relates to methods of administering the nanoparticles, e.g., in a suitable amount, manner, or mode of administration (e.g., a dose, dosage form, or mode of administration described herein). The method can be a method of treating a subject having a disorder.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about the nanoparticles therein and/or their use in the methods described herein. The informational material can also be provided in any combination of formats.

In addition to the nanoparticles, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit can include one or more containers for the nanoparticles or other agents. In some cases, the kit contains separate containers, dividers or compartments for the nanoparticles and informational material. For example, the nanoparticles can be contained in a bottle, vial, or syringe, and the informational material can be contained in a plastic sleeve or packet. In other situations, the separate elements of the kit are contained within a single, undivided container. For example, the nanoparticles can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of the nanoparticles. The containers can include a unit dosage, e.g., a unit that includes the nanoparticles. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of the nanoparticles, e.g., a syringe or other suitable delivery device. The device can be provided pre-loaded with nanoparticles, e.g., in a unit dose, or can be empty, but suitable for loading.

The invention is further illustrated by the following examples. The examples are provided for illustrative purposes only. They are not to be construed as limiting the scope or content of the invention in any way.

EXAMPLES

Example 1

Preparation of Nanoparticles of Paclitaxel and Atavoquone

Stable colloids of paclitaxel and/or atavoquone (two poorly soluble drugs) were prepared in order to increase their solubilization and their bioavailability.
A. Methods 5 mg paclitaxel or atavoquone was dissolved in 5 mL of a 60% ethanol/water or a 60% acetone/water solution in a glass tube. This solution was ultrasonicated at 100% amplitude for 2 min, and then 1 mL of a 5 mg/mL polylysine, polyethylenimine, or protomine sulphate solution was added. This was then ultrasonicated for 1 min while adding water at certain speeds and volumes (e.g., 1 mL/min until 5 mL to 10 mL was reached). This was then ultrasonicated for another 30 min. After sonication, the zeta potential of the sample was measured to assure recharging of the formed paclitaxel nanocrystals to positive. Layer-by-layer (LbL) coating with 2 layers of BSA/PS (bovine serum albumin/protamine sulfate) was performed (as described in, e.g., WO2009/012303), followed by SEM readings and measurement of zeta potential.

Figure 2:
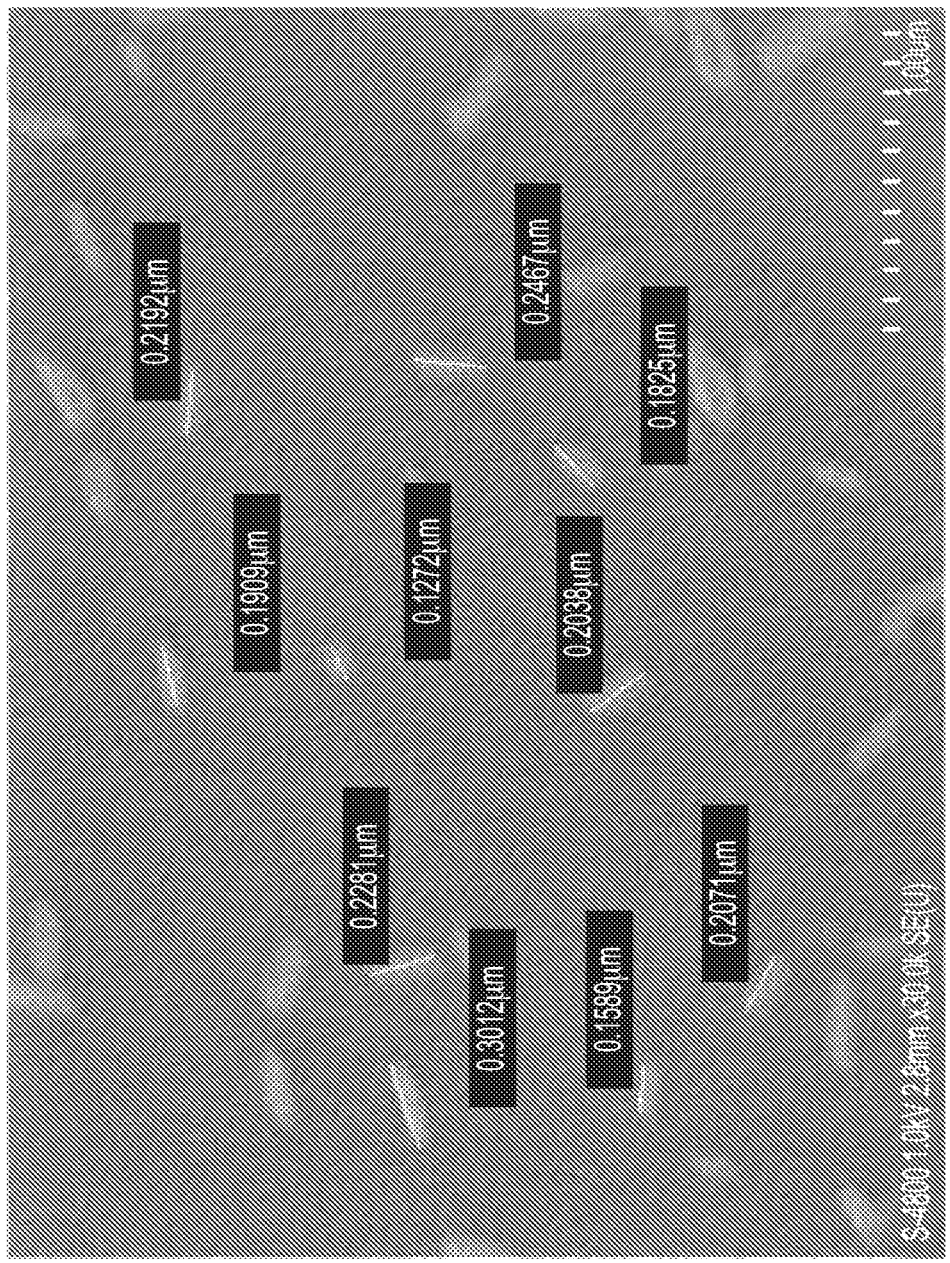
FIG. 2 is a representation of a scanning electron micrograph (SEM) of nanoparticles of paclitaxel coated with a layer of poly(lysine).

To produce mixed paclitaxel/atavoquone nanoparticles, 5 mg of paclitaxel and 5 mg of atavoquone were dissolved in 5 mL of a 60% ethanol/water solution. This solution was ultrasonicated at 100% amplitude for 2 min in a glass tube. 0.5 mL of a 5 mg/mL solution of polyethylenimine or polyallyamine was added. Water was added to the drug ethanol solution at a certain speed to reach a certain volume (e.g., 1 mL in min to a total volume 10 mL). SEM readings and zeta potentials were measured.
B. Results FIG. 2 shows an SEM image of about 90 nm×90 nm×200 nm rod-like particles of paclitaxel coated with poly(lysine). The initial solvent was acetone, the crystallization process was initiated, and nano-size paclitaxel particles coated with poly(lysine) were formed.

Figure 3A:
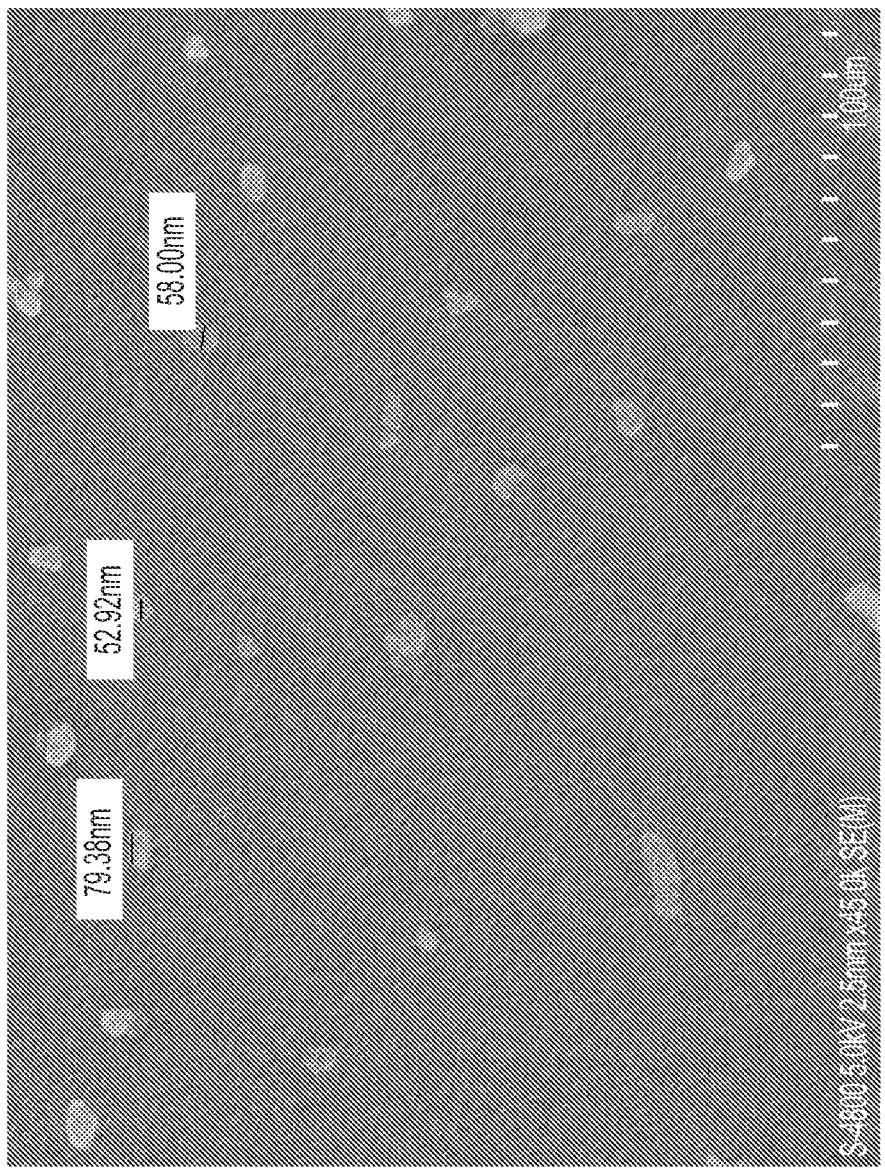
FIG. 3A is a representation of an SEM image of nanoparticles of paclitaxel in a 60% ethanol solution after ultrasonication in the presence of protamine sulfate (PS) for 15 min.
Figure 3B:
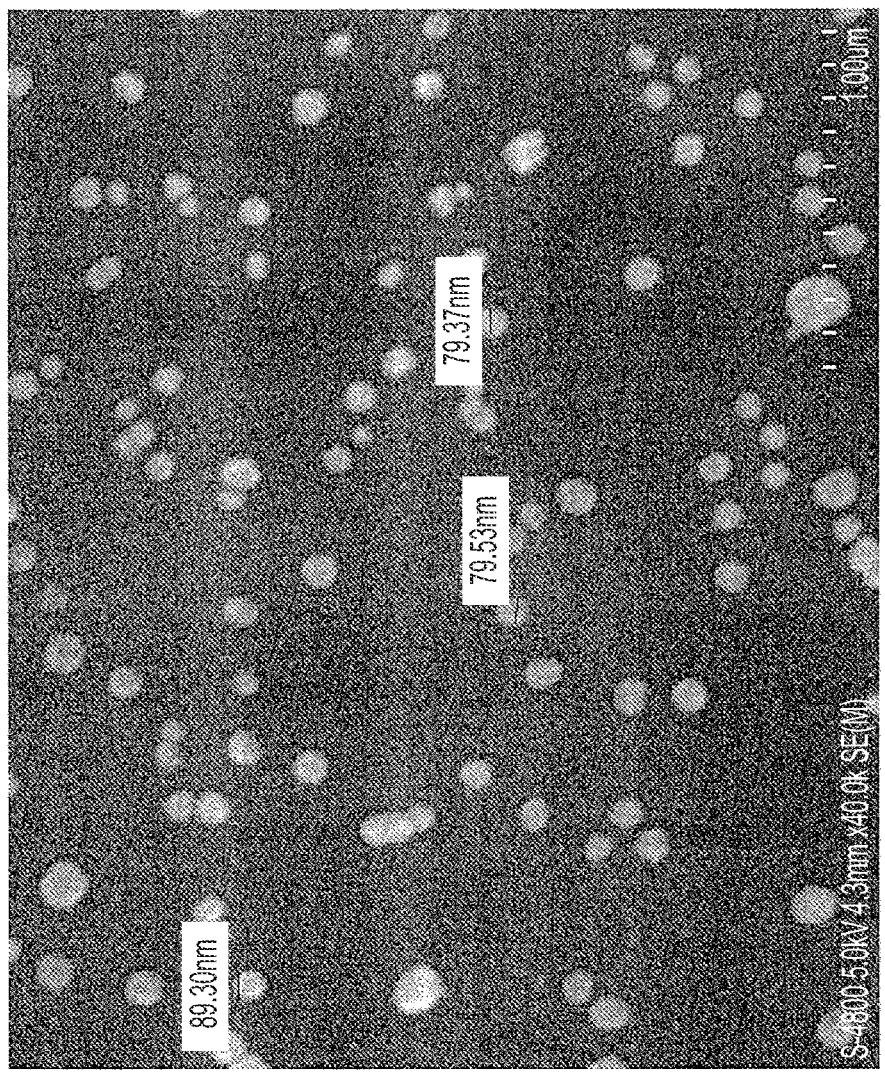
FIG. 3B is a representation of an SEM image of nanoparticles of paclitaxel in a 60% ethanol solution after ultrasonication in the presence of PS for 30 min.
Figure 3C:
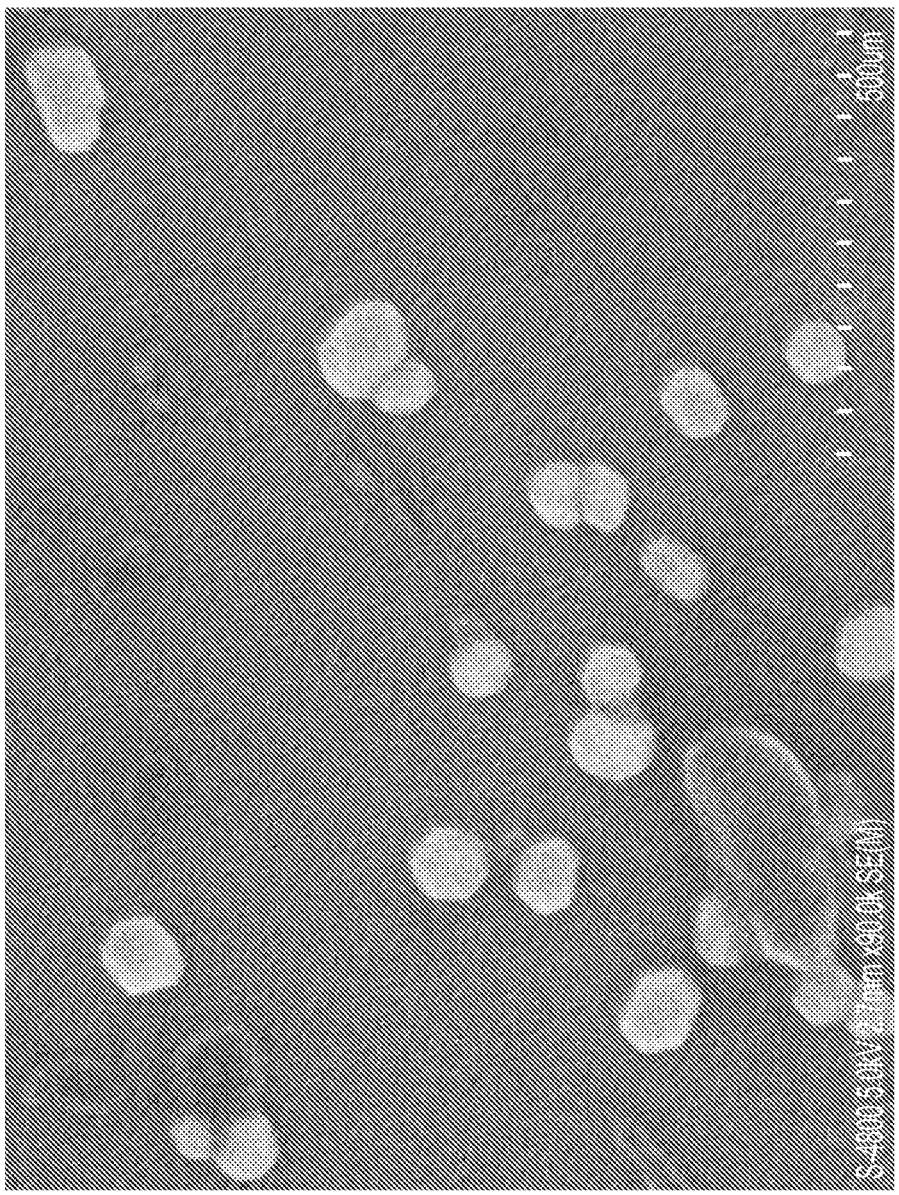
FIG. 3C is a representation of an SEM image of nanoparticles of paclitaxel in a 60% ethanol solution after ultrasonication in the presence of PS for 60 min.

FIG. 3 shows paclitaxel nanoparticle suspensions after 15 min (FIG. 3A), after 30 min (FIG. 3B) and after 60 min (FIG. 3C) sonication. Paclitaxel was initially dissolved in ethanol and protomine sulphate was added in the presence of ultrasonication. As shown in FIG. 3, the nanoparticles ranged in size from about 50 nm to about 90 nm in diameter.

Figure 4:
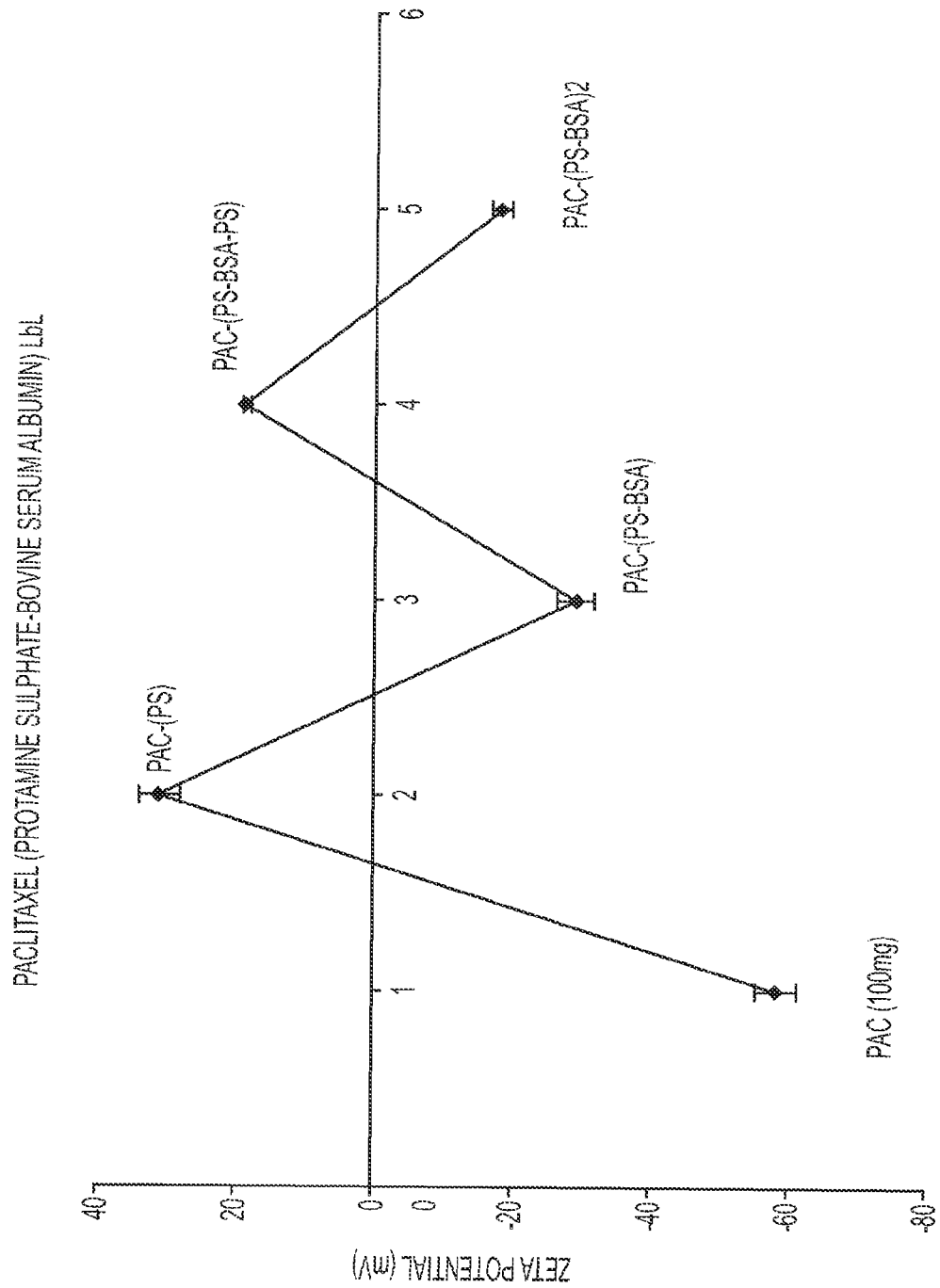
FIG. 4 is a graphic representation of the zeta potentials obtained from serial additions of PS or bovine serum albumin (BSA) onto paclitaxel nanoparticles.

FIG. 4 shows the changes in zeta potentials as alternate coatings of protamine sulphate (PS) and bovine serum albumin (BSA) were added to paclitaxel nanoparticles using a layer-by-layer method. After each coating, a sample was taken and surface potential was measured using a Zeta potential analyzer. As shown in FIG. 4, the initial paclitaxel compound was measured to be about −60 mV, and alternated to about +30 mV (after a first PS layer deposition), and then back to about −30 mV (after the first BSA layer deposition), then to about +20 mV (after deposition of the second layer of PS), and finally to about −20 mV (after deposition of the second layer of BSA).

Figure 5:
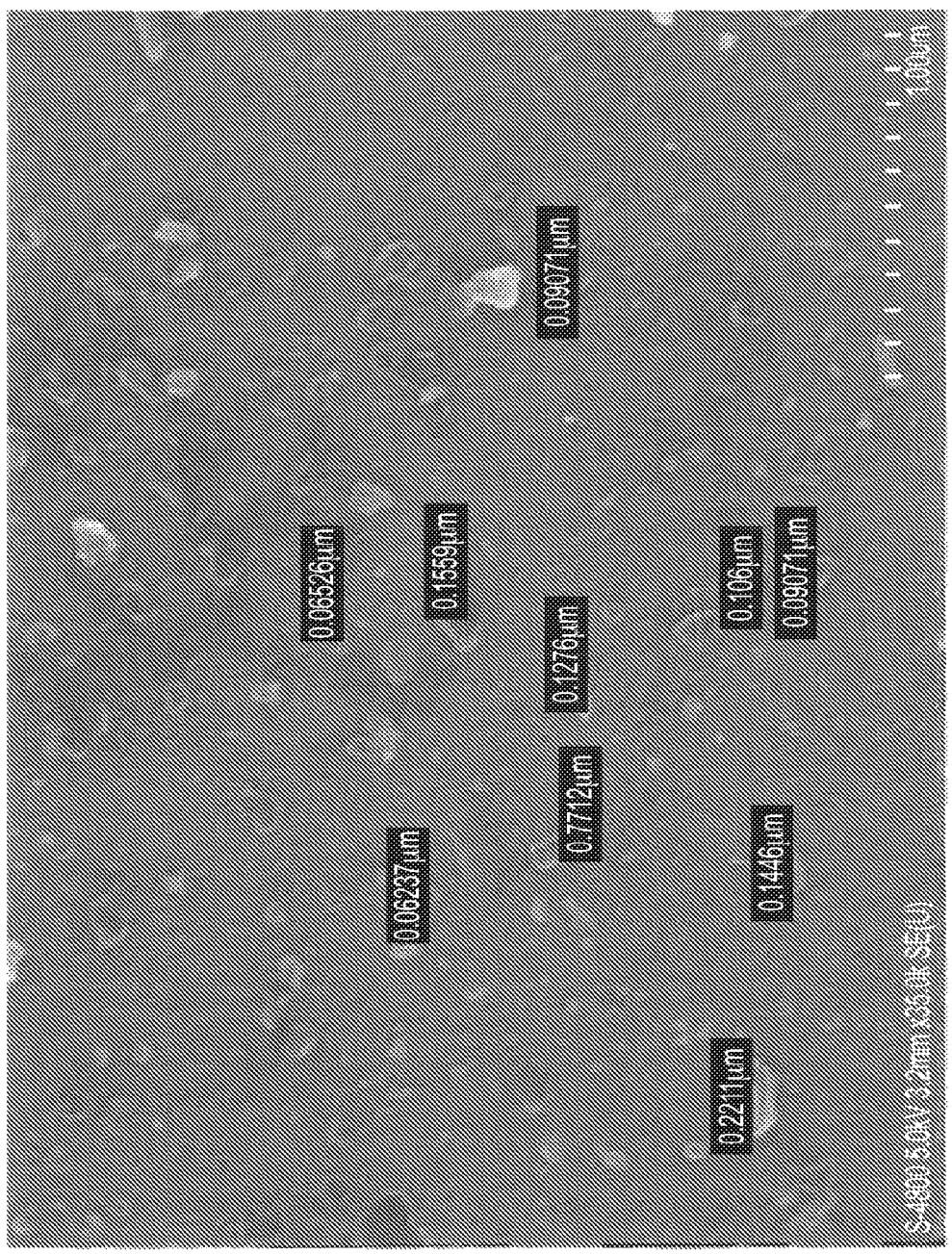
FIG. 5 is a representation of an SEM image of nanoparticles of atavoquone sonicated for 40 min with 1 mg/mL poly(allylamine) (PAH).

FIG. 5 shows an SEM image of atavoquone powder in 1 mg/mL cationic poly(allylamine) (PAH) sonicated for 40 min. This resulted in 120 nm±60 nm diameter stable colloids. The resulting particles coated with first layer of PAH had a zeta-potential of 4 mV to 20 mV, which was converted to about −30 mV, and after the second deposition of polyanion: polystyrene sulphonate (PSS).

When nanoparticles were formed from a mixture of paclitaxel and atavoquone were produces, the particles had a diameter of about 300 nm.
C. Summary of Results Water was added to a solution of paclitaxel and/or atavoquone in an organic solvent in the presence of ultrasonication. The water decreased the solvent concentration to microdroplets, and the solubility of the drug in the microdroplets decreased. The decrease of solubility initiated nucleation of the drug, thereby forming nanoparticles. The kinetics of nucleation varied by solvent type, concentration, pH, and temperature. The speed of adding water into the solvent also contributed to the particle size and shape. The formed nano-size crystals did not grow above nano-size, likely due to space confined conditions and/or ultrasonication. Simultaneous polyelectrolyte coating prevented the formed nanoparticles from re-aggregating. An LbL process was then used to add further layers of polyelectrolyte coatings to the nanoparticle.

Example 2

Preparation of Nanoparticles of Curcumin

Stable curcumin nanocolloids were formed through controlled crystallization initiated by worsening saturated curcumin alcohol solutions, as follows. Curcumin powder (Sabinsa Corp., East Windsor, N.J.). All other chemicals were obtained from Sigma-Aldrich. After curcumin was completely dissolved, aqueous polycations, poly(allylamine hydrochloride), PAH, or biodegradable protomine sulfate, (PS) were added, and ultrasonication was initiated using an UIP1000 Hielscher instrument (Hielscher USA, Inc., Ringwood, N.J.), at 100 Wt per mL of solution. During the sonication, water was slowly added into the solution. Upon the addition of water, the solvent became more polar, decreasing curcumin solubility. Eventually, the curcumin equilibrium concentration exceeded the solubility threshold, resulting in curcumin supersaturated conditions. Then, crystal nucleation started. Under high power ultrasonication, the drug particle growth was ceased at initial stages.

The adsorption of polyelectrolytes onto drug nanocrystals established a barrier to their further growth and aggregation. Obtained crystal particles were stable and did not aggregate after sonication was stopped. While not wishing to be bound by theory, aggregation may have been reduced due to the increase of surface charge provided by the adsorbed polyelectrolyte layer. After 45 min of sonication, curcumin nanocrystals were separated from solution by centrifugation and resuspended in deionized water. Additional polyelectrolyte multilayers were built on curcumin nanoparticles by alternate adsorption of polyanions and polycations (by LbL shell assembly as described in WO2009/012303).

Figure 6A:
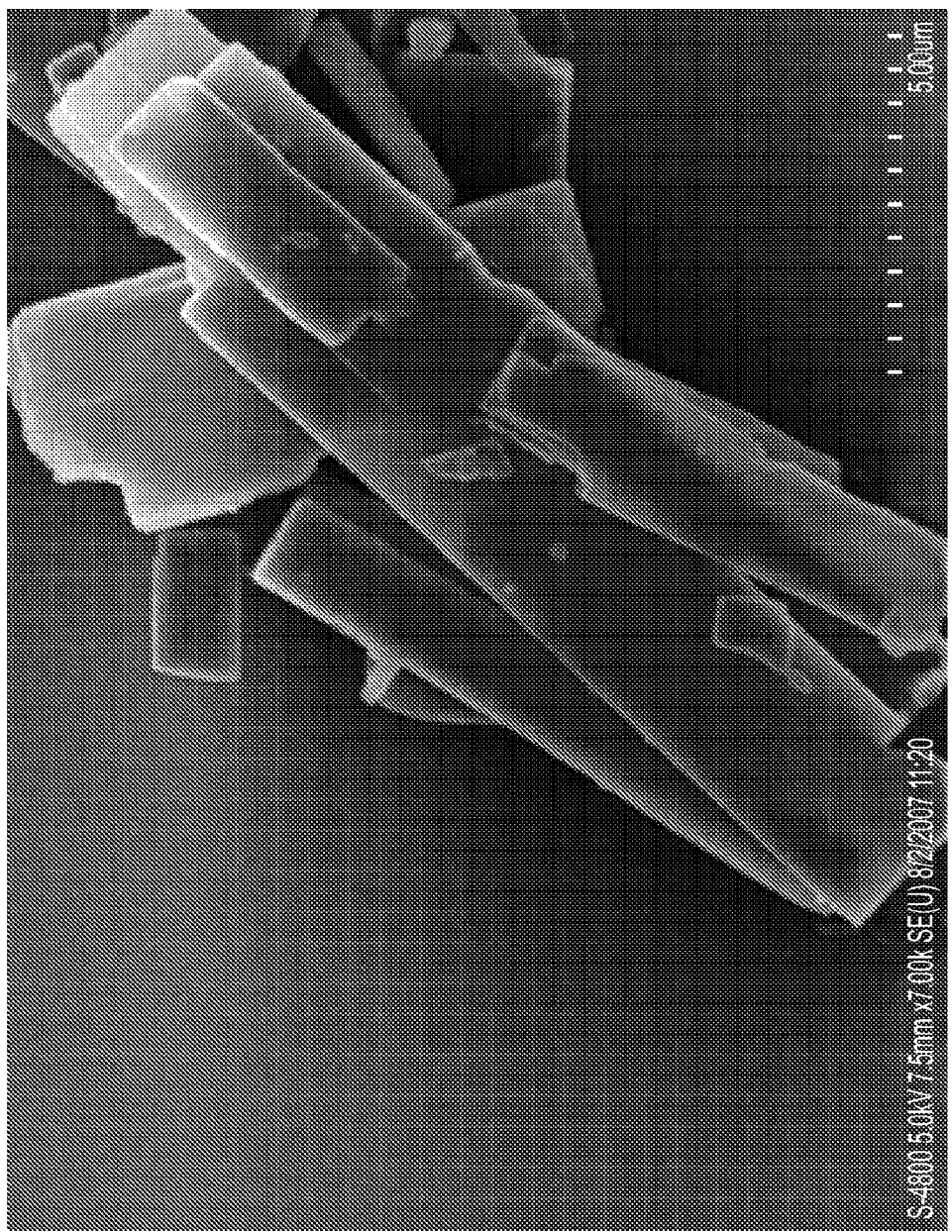
FIG. 6A is a representation of an SEM image of curcumin powder.
Figure 6B:
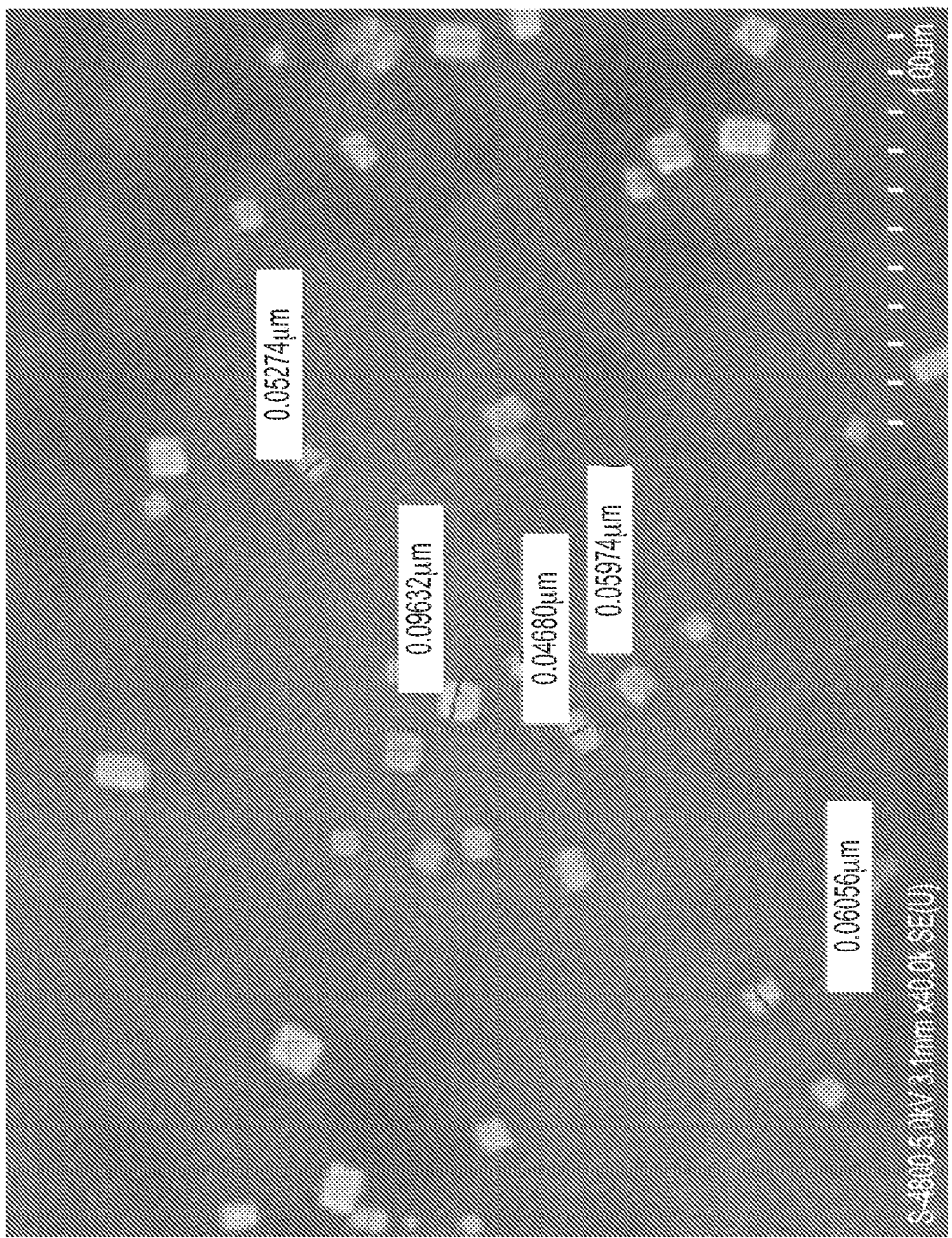
FIG. 6B is a representation of an SEM image of curcumin nanocolloids.
Figure 7:
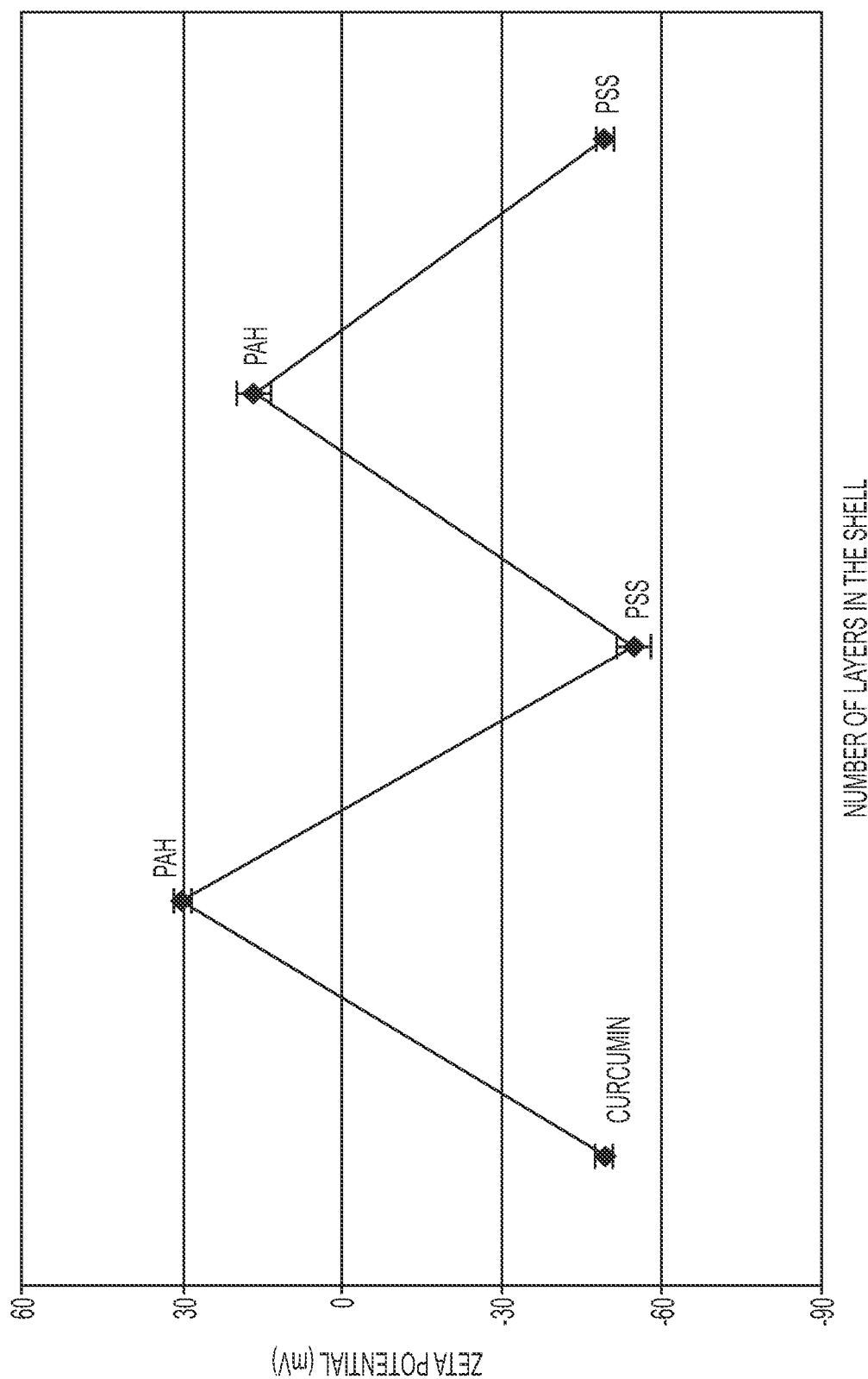
FIG. 7 is a graphic representation of the zeta potentials obtained from serial additions of poly(allylamine hydrochloride) (PAH) or sodium poly(styrene sulfonate) (PS) onto curcumin nanoparticles.

As shown in FIG. 6B, curcumin nanoparticles of square or rectangular shape were obtained having an average size of 80 nm±20 nm (estimated with SEM imaging (Hitachi) and light scattering experiments (Brookhaven Inc., ZetaPlus)). Due to the adsorption of cationic PAH, the surface potential of these nanoparticles was about +30 mV (FIG. 7). The high surface charge resulted in increased colloidal stability for this formulation. For example, a curcumin nanocolloid sample of 0.5 mg/mL drug concentration was preserved for two months as a stable dispersion. The rectangular shape of the nanoparticles was associated with the crystalline nature of the obtained curcumin nanoparticles.

To examine the crystal structure of the curcumin nanoparticles, X-ray powder diffraction analysis was carried out with a Bruker-D8 XRD instrument (Bruker AXS, Inc., Madison, Wis.). Bragg pick positions in the X-ray pattern obtained from dried nanoparticle powder coincided with the pick positions for bulk curcumin powder, but the picks were wider due to smaller crystallite sizes. These X-ray data indicate that the crystal structure of curcumin was preserved, and polycations added during drug crystal formation did not form a complex with curcumin.

To minimize the curcumin particle size, a series of samples were prepared that were processed under various conditions (e.g., different alcohol/water ratios, drug concentrations, ultrasonication power, time, and speed of the solvent worsening for crystallization initiation). Two factors that affected crystal size were the rate of water addition (speed of the solvent worsening) and the initial curcumin concentration. These two factors were optimized.

Figure 8A:
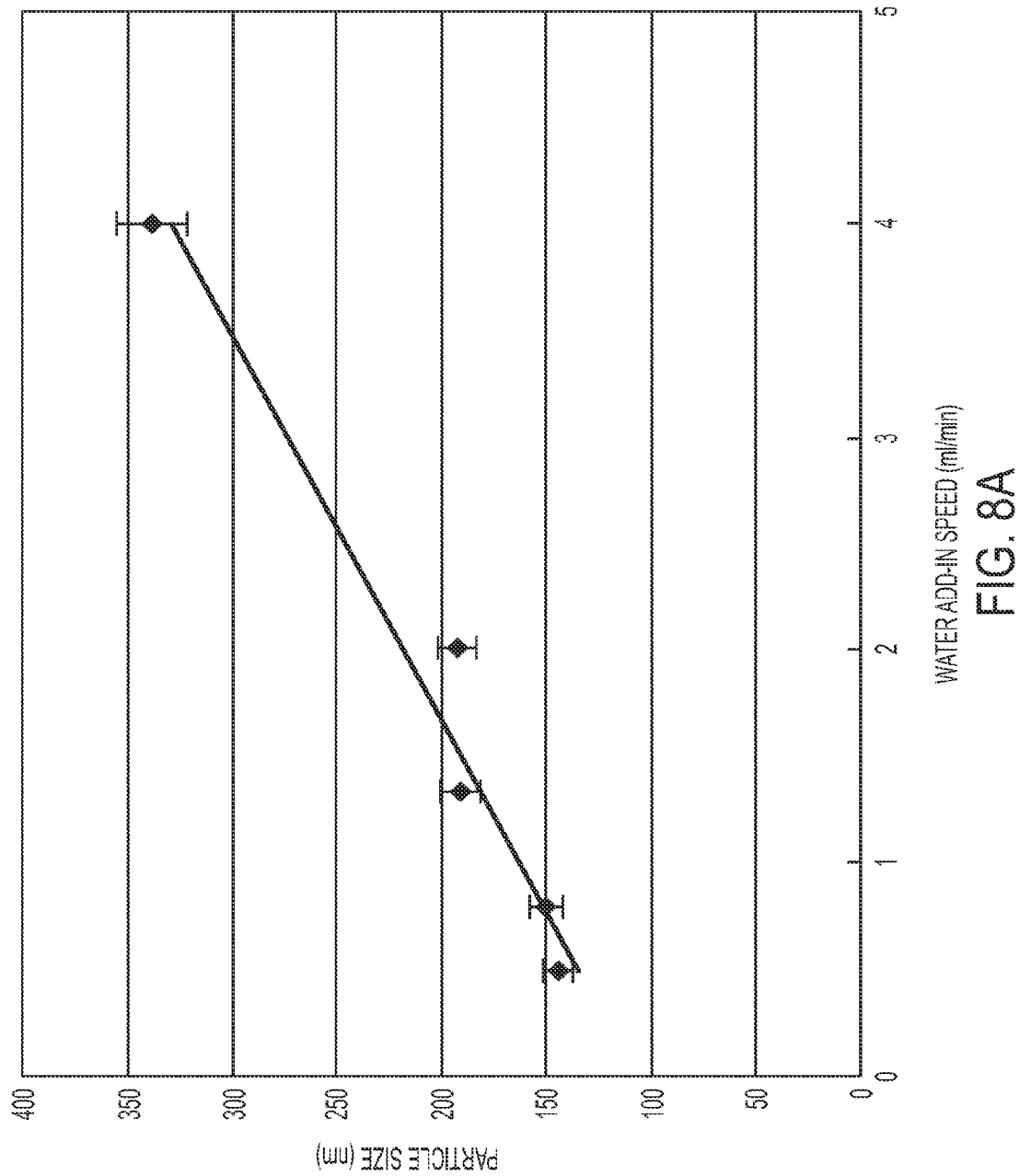
FIG. 8A is a graphic representation of the effect of the rate of adding water on particle size.
Figure 8B:
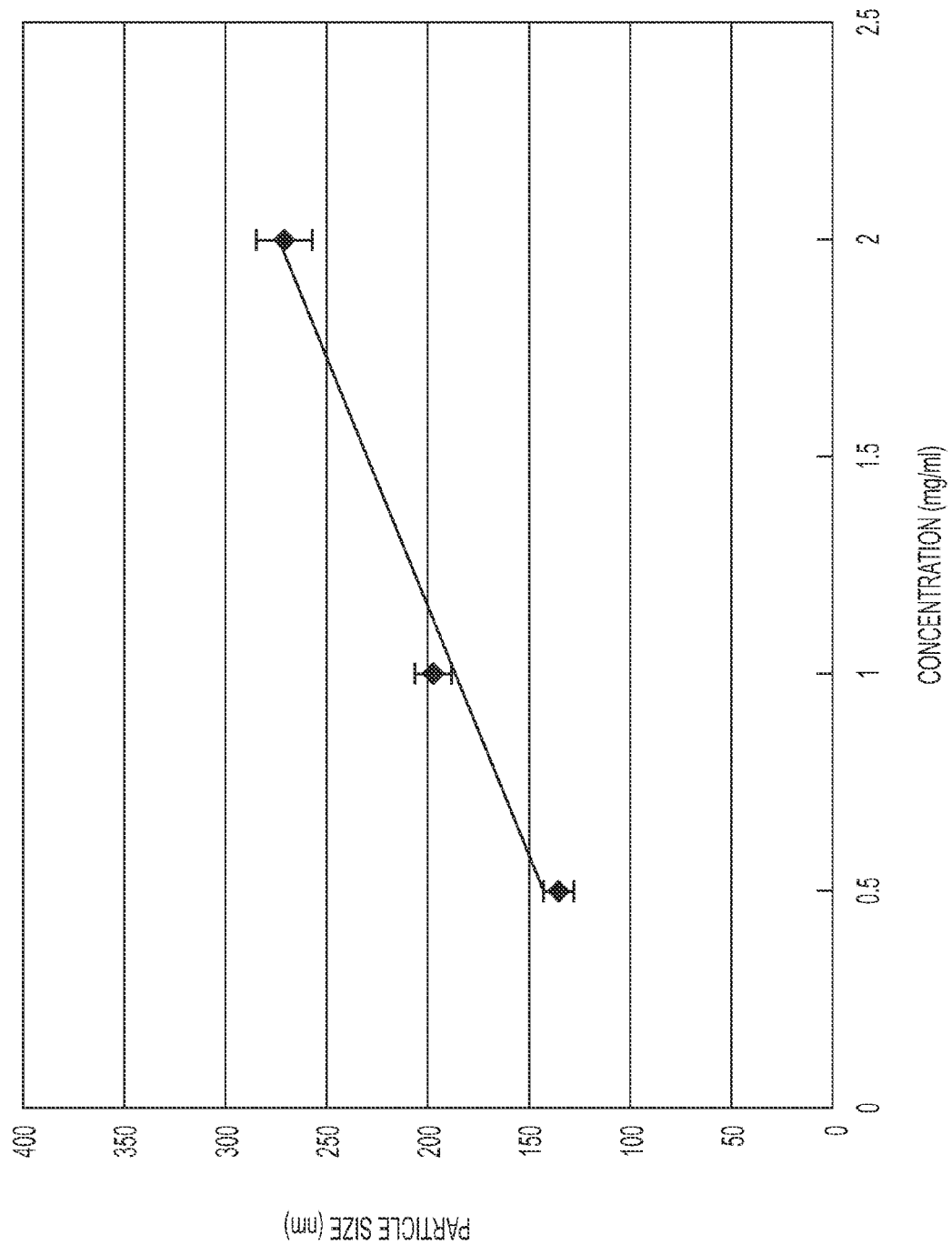
FIG. 8B is a graphic representation of the effect of curcumin concentration on particle size.

First, the water addition rate was varied from 0.05 mL/min to 0.4 mL/min for a sample volume of 50 mL. As shown in FIG. 8A, a higher rate of water addition resulted in the formation of larger particles. At a water addition rate of 0.4 mL/min, particles were formed having an average size of about 320 nm, while the addition of water at a rate of 0.05 mL/min, particles were formed having an average size of about 120 nm. When the initial concentration of curcumin was increased, larger nanoparticles were formed, as shown in FIG. 8B.

PAH and PSS were alternately added to the curcumin nanoparticles using the LbL procedure. Zeta potential measurements demonstrated that the LbL method resulted in the stepwise addition of PAH and PSS layers on curcumin nanoparticles. As shown in FIG. 7, bare curcumin microparticles had an initial potential of −50±2 mV. PAH adsorption during nanoparticles synthesis converted the potential to +30±2 mV. Next, anionic PSS adsorption changed the potential to −53±2 mV, followed by +19±2 mV with the addition of PAH, and again to −50±2 mV with the addition of PSS. Therefore, multiple layers of polycations and polyanions, i.e., (PAH/PSS)$_2$, were coated onto the curcumin nanoparticles.

Separate quartz crystal microbalance (QCM) analysis was performed on the curcumin nanoparticles upon the serial additions of polyelectrolytes using silver plated 9-MHz QCM resonators (USI-System Instr., Japan). The QCM analysis demonstrated a thickness increment of 2.0±0.3 nm for the PAH/PSS bilayer, and a total thickness of the two-bilayer shell on curcumin nanoparticles of about 4 nm.

To produce biocompatible nanoparticles, alternate adsorption of cationic protamine sulfate (PS) and anionic bovine serum albumin (BSA) were used. FIG. 6A shows the original curcumin crystals of approximately 2 μm×10 μm size. Curcumin was dissolved in 60% ethanol at a concentration of 2 mg/mL. Ultrasonication was applied for 45 min and water was added at a rate of 0.2 mL/min. For these LbL nanocapsules, zeta potentials also regularly alternated between +30 mV and −50 mV, providing high colloidal stability of the samples.

For curcumin nanoparticles made of PAH/PSS or PS/BSA shells, the curcumin nanoparticles had very thin coatings, resulting in high drug content of about 80-90%. This is in stark contrast to drugs loaded into micelle or liposome formulations, which typically have about 3-5% drug loading.

Figure 9:
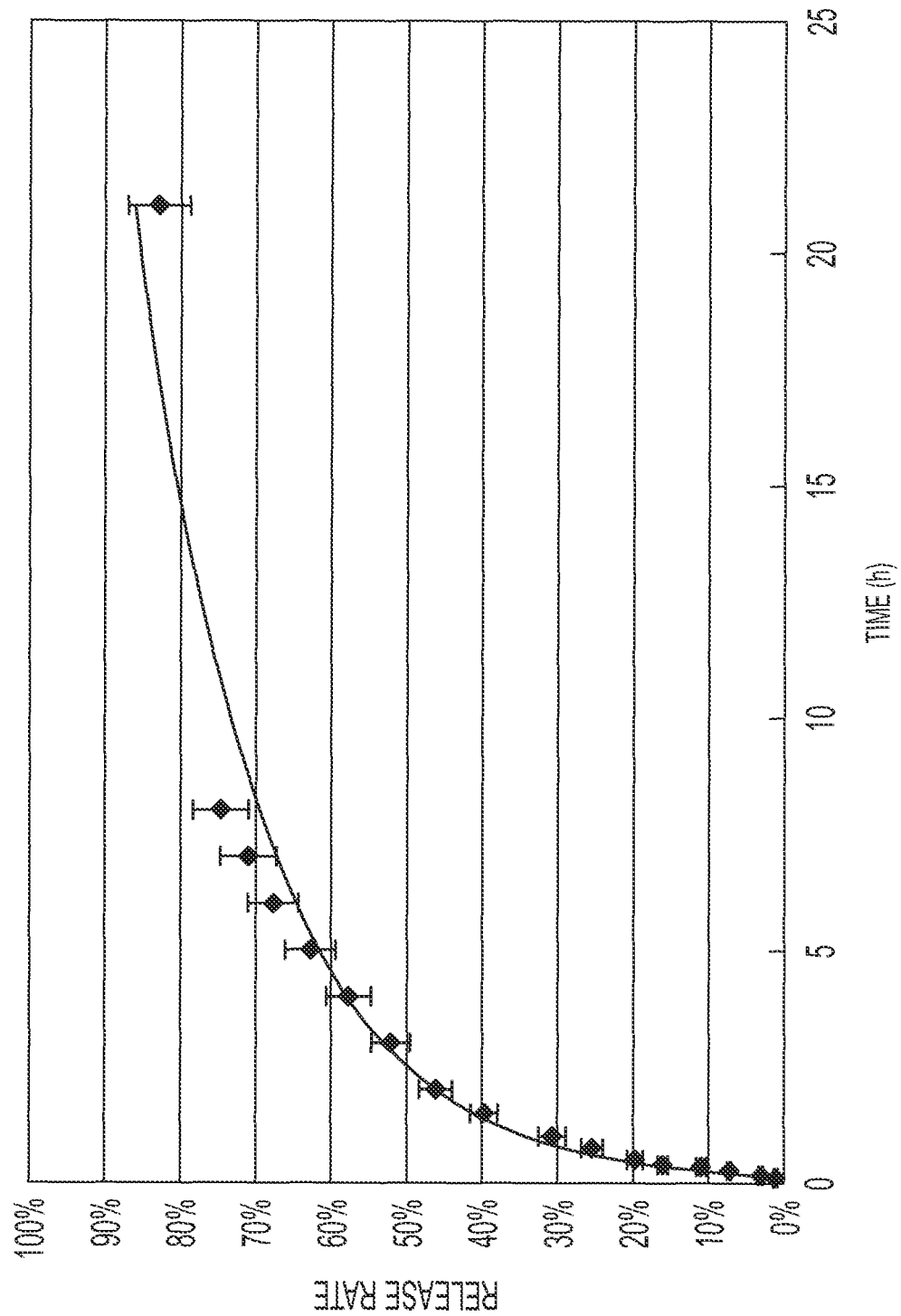
FIG. 9 is a graphic representation of the release of curcumin over time from curcumin-containing nanoparticles having (BSA/PS)$_2$ bilayers.

The drug release profile of the curcumin LbL-nanocolloids with the (BSA/PS)$_2$ coating was analyzed in a diffusion chamber (sink conditions). As shown in FIG. 9, 50% drug release was reached in about 3 hr. The release profile fit the Peppas model ($M_t/M_0 = K\exp(tn)$, where $M_t$ is the amount of drug released at time t, $M_0$ is the amount of drug released at infinite time, n is the exponent characteristic of the release mechanism, and K is a constant). The obtained n value of 0.5 indicated that the release mechanism was Fickian diffusion.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A stable nanoparticle comprising:
   a compound; and
   a polymeric coating comprising alternating polymeric layers of oppositely charged polymers,
   the nanoparticle having a diameter of about 20 nm to about 100 nm;
   wherein the oppositely charged polymeric layers each independently consist of a polymer selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

2. The nanoparticle of claim 1, wherein the compound is present at about 5% by weight to about 95% by weight; and
   wherein the nanoparticle does not contain a detergent or a surfactant.

3. The nanoparticle of claim 1, wherein the polymeric layers have a combined thickness of about 2 nm to about 10 nm; and
   wherein the nanoparticle does not contain a detergent or a surfactant.

4. A stable nanoparticle comprising:
   a compound;
   a first defined solid polymeric layer consisting of a first polymer, the first layer surrounding the compound; and
   a second defined solid polymeric layer consisting of a second polymer, the first polymer and the second polymer having opposite charges, and the second layer surrounding the first layer,
   the nanoparticle having a diameter of about 20 nm to about 100 nm;
   wherein the first and second polymers are each independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

5. The nanoparticle of claim 4, wherein the compound is present at about 5% by weight to about 95% by weight; and
   wherein the nanoparticle does not contain a detergent or a surfactant.

6. The nanoparticle of claim 4, wherein the first polymeric layer and the second polymeric layer have a combined thickness of about 2 nm to about 10 nm; and
   wherein the nanoparticle does not contain a detergent or a surfactant.

7. The nanoparticle of claim 4, comprising more than two defined, solid, polymeric layers;
   wherein the more than two defined, solid, polymeric layers each independently consist of a polymer selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

8. The nanoparticle of claim 4, further comprising a third polymeric layer surrounding the second polymeric layer, the third polymeric layer consisting of a third polymer having an opposite charge from the second polymer;

wherein the third polymer is independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly (alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly (hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

9. The nanoparticle of claim 8, wherein the first polymer and the third polymer are the same; and wherein the nanoparticle does not contain a detergent or a surfactant.

10. The nanoparticle of claim 8, further comprising a fourth polymeric layer surrounding the third polymeric layer, the fourth polymeric layer consisting of a polymer having an opposite charge from the third polymer;

wherein the fourth polymer is independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrvlic acid), poly (alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly (hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

11. The nanoparticle of claim 4, wherein the second polymeric layer is modified with a targeting agent; and wherein the nanoparticle does not contain a detergent or a surfactant.

12. The nanoparticle of claim 8, wherein the third polymeric layer is modified with a targeting agent; and wherein the nanoparticle does not contain a detergent or a surfactant.

13. The nanoparticle of claim 10, wherein the fourth polymeric layer is modified with a targeting agent; and wherein the nanoparticle does not contain a detergent or a surfactant.

14. The nanoparticle of claim 11, wherein the targeting agent is an antibody; and wherein the nanoparticle does not contain a detergent or a surfactant.

15. The nanoparticle of claim 4, wherein the compound is released from the nanoparticle at a rate of about 5% to about 50% within about two hours; and wherein the nanoparticle does not contain a detergent or a surfactant.

16. A method of making a stable nanoparticle, the method comprising:
- solubilizing a poorly soluble compound in an organic solvent;
- adding a first polymer in aqueous solution to the solubilized compound, the aqueous solution reducing the solubility of the compound in the organic solvent; and
- subjecting the compound to ultrasonication,
- the first polymer added at a concentration sufficient to form a stable first polymeric layer around the compound;
- wherein the first polymer is independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and
- wherein the nanoparticle does not contain a detergent or a surfactant.

17. The method of claim 16, further comprising adding water to the compound in the presence of the ultrasonication, resulting in crystal or amorphous nucleation of the compound; and
- wherein the nanoparticle does not contain a detergent or a surfactant.

18. The method of claim 17, further comprising adding a second polymer to the nanoparticle after the first polymeric layer is formed, thereby forming a second polymeric layer around the first polymeric layer;
- wherein the second polymer is independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride) (PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and
- wherein the nanoparticle does not contain a detergent or a surfactant.

19. The method of claim 18, further comprising adding a third polymer to the nanoparticle after the second polymeric layer is formed, thereby forming a third polymeric layer around the second polymeric layer;
- Wherein the third polymer is independently selected from the group consisting of acacia, acrylate gels, albumins, bovine serum albumin (BSA), human serum albumin (HSA), alginates, alginic acids, sodium alginate, cross-linked alginates, cellulose, carboxymethyl cellulose, cellulose derivatives, cellulose acetate, chondroitin sulfate, collagen, collagen derivatives, methylated collagen, succinylated collagen, cross-linked collagen, collagen-like proteins, chitosan, chitosan derivatives, methylpyrrolidone chitosan, dextran, dextran derivatives, dextran amine, dextran sulfate, carboxymethyl dextran, fibrin, gelatin, gelatine A, gelatin B, glycosaminoglycans, glycosoaminoglycan derivatives, graphite, glycolides, heparin, hyaluronic acid, cross-linked hyaluronic acid, keratin, lactides, myosin, nylon-2/nylon-6-copolyamides, poly casein, poly(acrylic acid), poly(alkylene succinates), poly(allylamine hydrochloride) (PAH), poly(allylamine), poly(butylene diglycolate), poly(cyanoacrylates), poly(aspartic acid), poly(d-aspartic acid), poly(l-aspartic acid), poly(dl-aspartic acid), polyglutamic acids, poly(d-glutamic acid), poly(l-glutamic acid), poly(dl-glutamic acid), polyarginine, polylysine, poly(dimethyldiallyammonim chloride), poly(dimethyldiallylamide ammonium chloride)

(PDDA), poly(ethylenimine), poly(glutaric acid), poly(hydroxy butyrate) (PHB), poly(lactide-co-glycolide), poly(ortho ester), polyanhydride, polycaprolactone, polyglycolic acid (PGA), polydihydropyrans, polyethylene glycol, polyglycolide, polyhydroxyalkonates, polylactic acid (PLA), polyesters, polypeptides, polynucleotides, polysaccharides, polysaccharide derivatives, polyoxalates, polyoxanones, polyphosphazenes, polytetrafluoroethylene, polyurethanes, polyvinylalcohol, polyvinylpyrrolidone, protamine sulfate (PS), copolymer of poly(bis(p-carboxyphenoxy)propane)anhydride (PCPP) and sebacic acid, copolymer of polylactic acid and polyglycolic acid (PLGA), silicone rubbers, silk-like proteins, silk-elastin-like proteins, starch, derivatives of starch, hydroxyethyl starch, substantially pure carbon lattices and combinations and copolymers thereof; and wherein the nanoparticle does not contain a detergent or a surfactant.

* * * * *

UNITED STATES PATENT AND TRADEMARK OFFICE
CERTIFICATE OF CORRECTION

PATENT NO. : 8,685,538 B2  
APPLICATION NO. : 13/259320  
DATED : April 1, 2014  
INVENTOR(S) : Torchilin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 78 days.

Signed and Sealed this

Twenty-ninth Day of September, 2015

Michelle K. Lee
*Director of the United States Patent and Trademark Office*